Figure 2A:
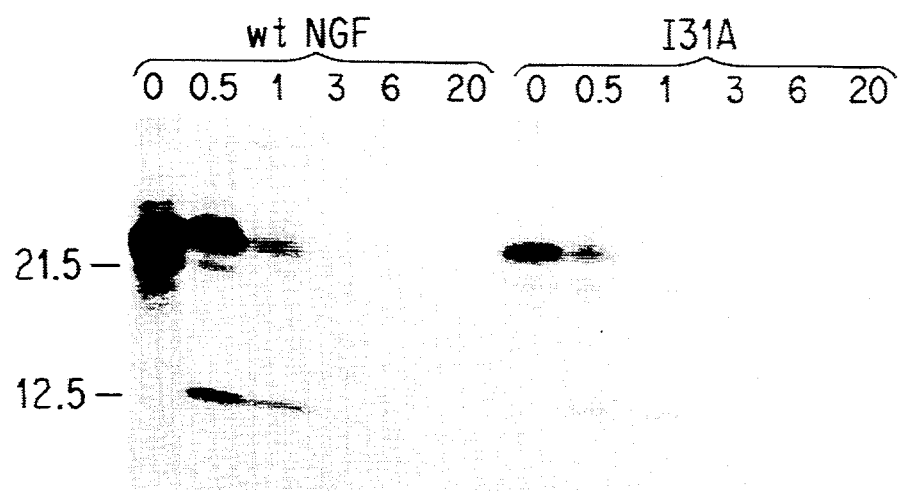

US005349055A

United States Patent [19]

Persson et al.

[11] Patent Number: 5,349,055
[45] Date of Patent: Sep. 20, 1994

[54] NERVE GROWTH FACTOR HAVING ALTERED RECEPTOR BINDING SPECIFICITIES

[76] Inventors: Hakan B. Persson, Vreta Gard, S-14743 Tumba, Sweden; Carlos F. I. Moliner, Tangvagen 29, S-12638 Hagersten, Sweden

[21] Appl. No.: 847,369

[22] Filed: Mar. 6, 1992

[51] Int. Cl.$^5$ .............................................. C07K 13/00

[52] U.S. Cl. ...................................... 530/399; 930/120

[58] Field of Search ................. 530/399, 387; 930/120

[56] References Cited

PUBLICATIONS

Berg et al. *Proc. Natl. Acad. Sci.* 88:7106–7110 (1991).

Ibanez et al. *EMBO J.* 9(5):1477–1483 (1990).

Ibanez et al. *EMBO J.* 10(8):2105–2110 (1991).

Loeb et al. *Cell* 66:961–966 (1991).

Meier et al. *EMBO J* 5(7):1489–1493 (1986).

*Primary Examiner*—Robert J. Hill, Jr.

*Assistant Examiner*—Shelly Guest Cermak

*Attorney, Agent, or Firm*—Gail M. Kempler

[57] ABSTRACT

A method of altering the receptor binding properties and the stability of neurotrophic factors is set forth. Mutant neurotrophic factors having altered receptor binding specificities are described. Specific embodiments include neurotrophic factors that bind trk receptors but do not bind to the low affinity NGF receptor.

8 Claims, 15 Drawing Sheets

```
               25         36
               KITATDIKGKEV
rat NGF        ............
mouse NGF      ............
human NGF      ............
bovine NGF     ............
guinea pig NGF ............
chicken NGF    ..K.........
xenopus NGF    ............
snake NGF      ..........NT.
```

FIG. 1A

```
              KITATDIKGKEV    KITATDIKGKEV
rat NGF                       .K..V.MS.GT.
rat BDNF                      ..S.I..R.HQ.
rat NT-3
xenopus NT-4                  .R..V.DR..I.
```

FIG. 1B

ND GROWTH FACTOR HAVING ALTERED RECEPTOR BINDING SPECIFICITIES

INTRODUCTION

The present invention provides mutant neurotrophic factors of the nerve growth factor family which have modified receptor binding affinity and biological specificity. It is based, in part, on the development of a model system which is useful for the rational design of analogues and chimeras of neurotrophic factors.

BACKGROUND OF THE INVENTION

The control of cell growth and differentiation requires specific factors which exert their effects via interaction with receptors on the surface of responsive cells. Despite the increasing number of growth and differentiation factors that have been discovered and characterized, the precise structures involved in binding and biological activity and the sequential and causal molecular events underlying the activation of multiple receptors are largely unknown.

Nerve growth factor (NGF)is a 118 amino acid polypeptide which controls the survival, development and differentiation of the sympathetic nervous system, as well as parts of the sensory and central nervous systems (Levi-Montalcini and Angeletti, 1968; Thoenen and Barde, 1980; Whittemore and Seiger, 1987; Thoenen et al., 1987). The biologically active form of NGF is a dimer of identical subunits each of which is produced from a precursor molecule (Angeletti and Bradshaw, 1971; Angeletti et al., 1973). A cDNA clone for NGF was first isolated in the mouse (Scott et al., 1983). Subsequently, the NGF gene has been characterized in a number of other species including several mammals, birds, reptiles and fishes (Schwarz et al., 1989; Hallböök et al., 1991).

NGF belongs to a family of structurally and functionally related molecules, collectively known as neurotrophins of the nerve growth factor family, which includes at least three other members, brain-derived neurotrophic factor (BDNF) (Barde et al., 1982; Leibrock et al., 1989), neurotrophin-3 (NT-3) (Hohn et al., 1990; Maisonpierre et al., 1990; Rosenthal et al., 1990; Ernfors et al., 1990) and neurotrophin-4 (NT-4) (Hallböök et al., 1991; Ip et al., 1992).

NGF interacts with a low-affinity receptor expressed on a variety of cell types of both neuronal and non-neuronal origin (Ernfors et al., 1988; Yan and Johnson, 1988; Heuer et al., 1990; Hallböök et al., 1990). The other three neurotrophins of the nerve growth factor family can also bind to the low-affinity NGF receptor (Rodriguez-Tébar et al., 1990; Ernfors et al., 1990; Squinto et al., 1991; Hallböök et al., 1991). This receptor is represented by a transmembrane glycoprotein of approximately 75,000 daltons ($p75^{NGFR}$) which binds NGF with a Kd of 10-9M (Johnson et al., 1986; Radeke et al., 1987). However, high affinity binding ($Kd=10^{-11}M$), restricted to a subpopulation of $p75^{NGFR}$-positive cells, is necessary to mediate the biological action of NGF. Banerjee et al., 1973; Herrup and Shooter, 1973; Sutter et al., 1979; Richardson et al., 1986). While the molecular relationship between the two receptor states is not entirely clear, several reports have indicated that the cytoplasmic domain of $p75^{NGFR}$ which lacks structural features known to mediate signal transduction in other receptors, is required for high-affinity binding and signal transduction (Hempstead et al., 1989; Yan et al., 1991; Berg et al., 1991).

It has recently been demonstrated that the proto-oncogene trk encodes a functional receptor for NGF (Kaplan et al., 1991a; Klein et al., 1991). The product of the trk proto-oncogene is a 140,000 dalton protein ($p140^{trk}$) which is a member of the tyrosine kinase family of transmembrane receptors (Martin-Zanca et al., 1991). Though it has been postulated that this protein participates in the primary signal transduction mechanism of NGF, there is considerable disagreement regarding the equilibrium binding constant of $p140^{trk}$ for NGF. Whereas Klein et al. (1991) reported that $p140^{trk}$ binds NGF with both low and high affinities, Kaplan et al (1991) and Hempstead et al (1991) reported that $p140^{trk}$ binds NGF with an affinity similar to that of $p75^{NGFR}$ and that coexpression for both receptors is required for high affinity binding to occur. Recently, the product of the trk proto-oncogene has been shown to constitute a functional receptor for NGF (Kaplan et al., 1991a; Klein et al., 1991). NGF binding to $p140^{trk}$ results in rapid phosphorylation of this molecule and stimulation of its tyrosine kinase activity (Kaplan et al., 1991a; Kaplan et al., 1991b; Klein et al., 1991).

In contrast, the role of $p75^{NGFR}$ in signal transduction has remained elusive. Recently, it was reported that the cytoplasmic domain of this receptor is involved in mediating neuronal differentiation (Yan et al., 1991) and NGF induced tyrosine phosphorylation (Berg et al., 1991) in PC12 cells. However, other recent studies have shown that polyclonal antibodies against $p75^{NGFR}$ abolish NGF binding to this molecule and some of the high-affinity binding but do not inhibit biological responses to NGF (Weskamp and Reichardt, 1991). Recent reports using cell lines expressing $p140^{trk}$ have demonstrated that in the presence of NGF this receptor molecule can mediate survival and mitotic proliferation of fibroblasts in the absence of $p75^{NGFR}$ (Cordon-Cardo et al., 1991). These studies could not rule out the possibility that binding to $p75^{NGFR}$ could be important in mediating NGF responses in neurons and neuron-like cell lines. It has also recently been shown that the trk proto-oncogene can rescue NGF responsiveness in mutant NGF-nonresponsive PC12 cell lines (Loeb et al., 1991). However, these cells still expressed substantial levels of $p75^{NGFR}$ therefore making it difficult to assess whether the presence of this molecule was required for the observed functional effects.

A better understanding of the molecular mechanism by which NGF exerts its biological effects is provided by the study of structure-function relationships and the creation of NGF mutants with altered properties. Initial studies along this line have analyzed the functional importance of highly conserved amino acid residues in the chicken NGF (Ibànez et al, 1990). More recently, an analysis of chimeric molecules between NGF and BDNF has delineated regions involved in determining the biological specificities of these two factors (Ibànez et al 1991a). Comparison of NGF genes from different species has revealed clusters of amino acid residues which are highly conserved across different groups of vertebrates (see FIG. 1, which demonstrates the conservation of amino acid residues 25 to 36 (single letter code) in NGFs from different species and in the homologous region of different neurotrophins. FIG. 1A shows alignment of residues 25 to 36 from rat (SEQ ID NO: 1) (Whittemore et al., 1988), mouse (SEQ ID NO: 1) (Scott et al., 1983), human (SEQ ID NO: 1) (Ullrich et al., 1983), bovine (SEQ ID NO: 1) (Meier et al., 1986), guinea pig (SEQ ID NO: 1) (Schwarz et al., 1989), chicken (SEQ ID NO: 1) (Ebendal et al., 1986; Meier et al., 1986), xenopus (SEQ ID NO: 2) (ref) and snake (SEQ ID NO: 3) (Selby et al., 1987) NGF. FIG. 1B shows alignment of residues 25 to 36 from rat NGF (SEQ ID NO: 1) and the homologous residues of rat BDNF (SEQ ID NO: 4) (Maisonpierre et al., 1990), rat NT-3 (SEQ ID NO: 5) (Maisonpierre et al., 1990; Ernfors et al., 1990) and xenopus NT-4 (SEQ ID NO: 6) (Hallböök et al., 1991).

Among these conserved parts, the region panning residues 25 to 36 is the most hydrophilic and therefore likely to be on the surface of the NGF molecule (Meier et al., 1986; Ebendal et al., 1989). Synthetic peptides designed from this sequence have been shown to inhibit the in vitro biological activity of NGF (Longo et al., 1990).

SUMMARY OF THE INVENTION

The present invention provides mutant neurotrophic molecules of the nerve growth factor family which have novel receptor binding affinities and specificities as compared to their parent molecules. The invention is based, in part, on the use of NGF as a model system to determine the role of specific amino acids in the binding of the molecule to both the $p75^{NGFR}$ and the $p140^{trk}$ receptor. The present invention is based on the further discovery, using such model systems, that modifications can be made to NGF that result in loss of the ability of the molecule to bind to $p75^{NGFR}$ while maintaining the ability of the molecule to bind to $p140^{trk}$ and to exhibit biological activity comparable to the wild-type molecule. In various embodiments, modifications made to NGF as well as to corresponding regions in other members of the nerve growth factor family result in neurotrophic factors with greater specificity to the trk signal transducing receptors.

DESCRIPTION OF THE FIGURES

FIG. 1A and 1B. Comparison of amino acid residues 25 to 36 (single letter code): A) in NGFs from different species; and B) members of the NGF family.

FIG. 2A, 2B, and 2C Stability of parent and mutant NGF in COS cells as measured by: A and B) pulse chase experiments using immunoprecipitation and SDS-PAGE; and C) induction of c-fos mRNA.

FIG. 3A and 3B Effect of the E35A mutation on the processing of the NGF propeptide as measured by A) immunoprecipitation and SDS-PAGE; and B) pulse chase experiments.

FIG. 4A, 4B, and 4C Competitive receptor binding (FIG. 4A) and biological activities neurite outgrowth, of FIG. 4B; and induction of c-fos mRNA, FIG. 4C, of the parent(wt) and mutant NGF.

FIG. 5A, 5B, and 5C. Biological activities in PC12 cells of parent NGF and NGF mutants deficient in low-affinity receptor binding as measured by A) neurite outgrowth in PC12 cells; B) neurite outgrowth over time; and C) induction of c-fos mRNA over time.

FIG. 6. Competitive receptor binding of parent NGF and NGF mutants in A) A875 cells; and B) r trk-3T3 cells.

FIG. 7. Effect of the K95A mutation on receptor binding of NGF to receptors on A) PC12 cells; B) A875 cells; and C) r trk-3T3cells.

FIG. 8A and 8B Biological activities [A) neurite outgrowth and B) neuronal survival] in sympathetic neurons of parent NGF and NGF mutants deficient in binding to $p75^{NGFR}$.

FIG. 9A, 9B, and 9C Functional dissection of the receptor binding site of NGF to $p75^{NGFR}$.

DETAILED DESCRIPTION OF THE INVENTION

Nerve growth factor (NGF), like many other growth factors and hormones, binds to two different receptor molecules on the membrane of responsive cells. The product of the proto-oncogene trk, $p140^{trk}$, is a tyrosine kinase receptor that has recently been identified as a signal transducing receptor for NGF. The role of the low-affinity NGF receptor, $p75^{NGFR}$, in signal transduction is less clear. The crystal structure of NGF has recently been determined, although the structures involved in receptor binding and biological activity are still unknown.

Site-directed mutagenesis combined with binding and biological assays provides a valuable tool to assess the functional importance of amino acid residues associated with the binding of neurotrophic molecules. Such studies, combined with the resolution of the three-dimensional crystal structure of NGF (McDonald et al., 1991) enables the rational design of neurotrophic molecules with altered receptor binding properties.

Accordingly, the present invention is directed to novel, mutant neurotrophic factors that are created by modifying one or more amino acids in the parent or wild-type neurotrophic factor of the nerve growth factor family. Such modifications are selected so as to reduce binding of the factor to the low affinity NGF receptor while maintaining the ability of the factor to bind to a trk receptor.

As contemplated herein, modification of specific amino acid residues alters the specificity of the NGF. Based on the three dimensional structure of NGF, it has been determined that these alterations are in amino acid residues in a $\beta$-hairpin loop exposed on the outside arm of the NGF dimer (McDonald et al., 1991). As described herein, residues with a positively charged side-chain within this region appear to be responsible for the main contact between NGF and $p75^{NGFR}$.

Applicants have discovered that NGF molecules mutated in these positions do not bind to the $p75^{NGFR}$ but retain binding to the trk proto-oncogene product and biological activity. These results suggest that $p140^{trk}$ alone is sufficient, at least in culture, to mediate biological activity of NGF in neuronal cells. Experiments conducted using mutated NGFs show that binding to $p75^{NGFR}$ is not required for induction of early gene expression, such as c-fos, or for neuronal differentiation of PC12 cells. Moreover, neither neurite outgrowth nor neuronal survival of cultured sympathetic neurons, which express both $p75^{NGFR}$ mRNA and protein (Ernfors et al., 1988; Yan and Johnson, 1988) and trk mRNA (G. Barbany, unpublished), was affected by the loss of binding to $p75^{NGFR}$. These results demonstrate, for the first time, that the trk proto-oncogene product alone is sufficient to mediate a response to NGF in cultured neuronal cells, thus opening up unique possibilities to unravel the role of both $p75^{NGFR}$ and $p140^{trk}$ in mediating the biological activities of NGF and to create unique neurotrophic molecules with improved binding specificities.

Although it may be possible that, in the mutants described herein, NGF binds through a different binding site to a new pocket created by an heterodimer of p75$^{NGFR}$ and p140$^{trk}$ (Hempstead et al., 1991) or, alternatively, free p75$^{NGFR}$ could still contact complex NGF-p140$^{trk}$ and in this way cooperate in signal transduction, p75$^{NGFR}$-p140$^{trk}$ complexes have not been detected in cross-linking experiments performed with either PC12 cells or sensory neurons under conditions which allowed detection of p75$^{NGFR}$ or p140trk homodimers (Meakin and Shooter, 1991). The fact that the mutant molecules of the present invention retain binding to p140trk strongly argues for the fact that the observed biological activities were mediated by this receptor molecule alone.

Although not intended to limiting, it is postulated herein that in certain neurotrophins of the nerve growth factor family, namely NGF, NT-3 and NT-4, the positively charged amino acids in the β-hairpin loop 30 to 34 play a significant role in the ability of the molecules to bind to p75$^{NGFR}$. Thus, according to one embodiment of the invention, alterations are made in one or several of these amino acids such that the overall charge in this region is altered, thereby reducing the ability of the molecule to bind to p75$^{LNGF}$ while maintaining the ability of the molecules to bind to their corresponding trk receptors. As used herein, amino acid residue 1 is the first amino acid in the mature protein.

In one such embodiment, the positively charged side chain of Lys32 is replaced by, for instance the methyl group of Ala. Such reduction reduces the binding of the molecule to p75$^{NGFR}$ to 5% of the binding seen with parent NGF (Table 2 and FIG. 6). In another embodiment, the change of Lys34 into Ala reduces binding to A875 cells to 55% of the parent levels. In yet another embodiment, the simultaneous replacement of Lys32, Lys34 and Glu35 by alanine is used to completely abolish the binding of the mutant molecule to p75$^{NGFR}$. In the case of each of these mutants, despite reduced or absent binding to p75$^{NGFR}$, the molecules retain wild-type biological activity on explants of sympathetic ganglia.

In an additional embodiment, mutant neurotrophic factors are designed based on the discovery that positively charged amino acids around amino acid 95 in a second β-hairpin loop may interact with Lys32 and Lys34 to form a positively charged interface involved in binding to p75$^{NGFR}$. Simultaneous modification of Lys32 with either of the two other lysines (Lys 34 or Lys 95) results in loss of binding to p75$^{NGFR}$. Despite the lack of binding to p75$^{NGFR}$, these mutants bind to p140$^{trk}$ and retain their biological activity, as measured by neuronal differentiation of PC12 cells and survival of cultured sympathetic neurons.

Because the other three known neurotrophins can also bind to the low-affinity NGF receptor (Rodriguez-Tébar et al., 1990; Ernfors et al., 1990; Squinto et al., 1991; Hallböök et al., 1991), comparable changes in the corresponding amino acids would be expected to result in comparable alterations is binding specificity while not affecting the ability of these molecules to bind to their respective signal transducing trk receptor. Lys95 is conserved in all four proteins described so far (in Xenopus NT-4, the amino acid in position 95 is Lys, whereas in human NT-4 positions 94 and 96 are the positively charged amino acids glutamine and arginine). Further, in NT-3 and NT-4, Lys32 is replaced by Arg. Lys34 is also conserved in NT-4. Accordingly, alteration in any of these positively charged amino acids (e.g. by replacing the positively charged amino acid by a neutral, or negatively charged amino acid) to lower the binding to p75$^{NGFR}$ would be contemplated by the present invention.

The present invention also includes altered molecules wherein other modifications to the β-loop region around Lys95 are made. For example, in BDNF, Lys32 and Lys34 are replaced by Ser and Gly, respectively. Interestingly, the spatially close loop of residues 93 to 96 in BDNF has three consecutive positively charged residues (two lysines and an arginine) that may compensate for the absence of Lys32 and Lys34. A chimeric NGF molecule which has residues 23 to 35 (variable region I) replaced by the corresponding residues in BDNF (Ibànez et al., 1991a) showed a 10-fold reduction of low affinity binding to PC12 cells. The low affinity binding was restored in another chimeric molecule that contains both variable region I and residues 94 to 98 (variable region V) from BDNF, indicating that the three positively charged residues at positions 95, 96 and 97 in BDNF can compensate for the lack of Lys32 and Lys34. Although both NGF and BDNF appear to equally compete for binding to p75$^{NGFR}$, this receptor also recognizes differences between the two ligands which are reflected, in the case of BDNF, by positive cooperativity and slower dissociation kinetics (Rodriguez-Tébar et al., 1990). It therefore appears that BDNF and NGF are recognized by p75$^{NGFR}$ as similar albeit not identical structures. The results described herein provide a structural explanation for the observed differences between NGF and BDNF and suggest that other neurotrophins may interact with p75$^{NGFR}$ through the same region.

Also embodied herein are modifications of parent neurotrophic factors to enhance their stability. As described herein, selective modification of one or more of the amino acid residues occurring between amino acid 25 and 36 of neurotrophic factors of the nerve growth factor family appears to alter the stability of the factors. Accordingly, the invention contemplates alteration of such amino acids, followed by measuring the stability and biological activity of the altered molecule to select those factors that retain their biological activity but have enhanced stability as compared to the parent molecule.

The present invention, which relates to second generation factors derived from neurotrophic factors such as NGF, BDNF, NT-3 and NT-4, may be utilized to treat diseases in essentially the same way as the parent factors are utilized. For instance, they may be utilized to treat diseases and disorders of the nervous system which may be associated with alterations in the pattern of neurotrophic factor expression or which may benefit from exposure to the neurotrophic factor.

With respect to factors produced according to the present invention that do not bind to p75$^{NGFR}$, such molecules may have increased specificity toward target cells and therefore be effective in lower dosages. Further, such molecules may produce less side effects than the parent molecules, which bind to a more widely distributed array of neuronal cells. Retrograde transport, presumed to be mediated by p75$^{NGFR}$, could be prevented by the use of mutated neurotrophins thereby allowing a local effect of mutated neurotrophins in defined areas of the brain where their high-affinity receptors are expressed (such as in the hippocampus, following brain insults).

Materials and Methods

The following experimental procedures were used throughout the experiments described herein.

DNA cloning and site-directed mutagenesis

A 770 base pair EcoRI fragment containing the pre-proNGF coding sequence from the rat NGF gene (Whittemore et al., 1988) was cloned into pBS KS+ (Stratagene). Single stranded DNA from this plasmid was used as template for oligonucleotide based site-directed mutagenesis as described by Kunkel et al. (1985) and detailed in Ibànez et al. (1990). The replacements were confirmed by nucleotide sequence analysis by the chain-termination method (Sanger et al., 1977). For protein expression, DNA inserts containing the desired replacements were then subcloned in pXM (Yang et al., 1986).

Production and quantitation of recombinant proteins

COS cells grown to about 70% confluency were transfected with 25 μg plasmid DNA per 100 mm dish using the DEAE dextranchloroquine protocol (Luthman and Magnusson, 1983). To correct for differences in the amounts of recombinant protein produced by the different constructs, 35 mm dishes transfected in parallel were grown in the presence of 100 μCi/ml $^{35}$S-cysteine (Amersham). Aliquots of conditioned media were then analyzed by SDS/PAGE and the amounts of recombinant protein in the different samples were equilibrated after densitometer scanning of the corresponding autoradiograms as previously described (Ibànez et al., 1991b). The absolute amount of parent NGF protein was assessed by quantitative immunoblotting of conditioned media and by measurement of biological activity in cultured sympathetic ganglia using standards of purified mouse NGF (Ibànez et al., 1990; Ibànez et al., 1991b). The data obtained from these analysis were then used to determine the protein concentration in the samples containing mutant proteins.

Pulse-chase and immunoprecipitation

Forty eight hours after transfection cells were incubated in cysteine-free media for 4 hours. The cells were then pulse-labeled with 1 mCi/ml of $^{35}$S-cysteine during 15 min. The chase was performed by replacing the labeling media with complete medium fortified with 2 mg/ml of cold cysteine. Parallel wells were harvested at different times and cell extracts and conditioned media were immunoprecipitated with a polyclonal rabbit antiserum (rabbit no. 30) against mouse NGF (Ebendal et al., 1989) and analyzed by SDS/PAGE under reducing conditions as previously described (Ibanez et al., 1990; Ibánez et al., 1991b).

Binding assays

Mouse NGF was labeled with $^{125}$I by the chloramine-T method to an average specific activity of $3 \times 10^7$ cpm/μg. Rat PC12 cells (Greene and Tischler, 1976), human A875 cells (Buxser et al., 1983) and mouse rtrk-3T3 cells (Kaplan et al., 1991a) were used at 2 to $10 \times 10^6$ cells/ml. Steady state binding was measured in competition assays performed at 37° C. using $1.5 \times 10^{-9}$M $^{125}$I-NGF and serial dilutions of conditioned media containing equivalent amounts of parent or mutated NGF protein. All components were added at the same time and the cells were collected by centrifugation after equilibrium was reached (1-2 hours incubation). Control experiments using medium from mock transfected COS cells showed that other proteins present in the conditioned medium had no effect on the binding of $^{125}$I-NGF to the cells. Nonspecific binding was measured in a parallel incubation to which at least a 1000-fold molar excess of unlabelled NGF was added. All results were corrected for this nonspecific binding, which was always less than 10% of total binding. The concentration of each mutant and wild type NGF that gave 50% binding ($IC_{50}$) was determined, and relative binding was calculated using the relationship: (mutant $IC_{50}$/wild type $IC_{50}$) × 100.

Biological assays

Serial dilutions of conditioned media containing equivalent amounts of recombinant protein (in the range of 0.2 to 20 ng/ml) were assayed for biological activity on explanted chick embryonic day 9 sympathetic ganglia as previously described (Ebendal, 1984; Ebendal, 1989). Fibre outgrowth was scored on a semi-quantitative scale in biological units (BU) by comparison to standards obtained with purified mouse NGF, for which 1 BU is equivalent to approximately 5 ng/ml. The concentration of each NGF protein that gave 0.5 BU in this scale was determined, and used to calculate the relative activity compared to that obtained with parent NGF.

PC12 cells plated in 35 mm wells coated with poly-D-lysine were incubated with serial dilutions of conditioned media containing equivalent amounts of recombinant protein. At different time intervals, the percentage of cells bearing fibers longer than two cell diameter was determined microscopically.

Induction of c-fos mRNA was measured by quantitative Northern blot analysis of total mRNA from PC12 cells treated with dilutions of conditioned media containing equivalent amounts of recombinant parent and mutant NGF. Total RNA was extracted as previously described (Ibánez et al., 1990). Ten μg of total RNA was electrophoresed in a 1% agarose gel containing 0.7% formaldehyde and transferred to nitrocellulose membranes. The filters were then hybridized with a $\alpha$-$^{32}$P-dCTP radiolabelled rat c-fos gene fragment (Curran et al., 1987) and washed at high stringency. The amount of c-fos mRNA was determined by densitometer scanning of autoradiograms.

Dissociated neurons of the superior cervical ganglion from post-natal day 1 rats were cultured in 35 mm wells coated with poly-D-lysine at a density of 30,000 cells/well. Serial dilutions of conditioned media containing equivalent amounts of recombinant protein were added at the time of plating and neuronal survival was determined after 72 hours by phase contrast microscopy.

EXAMPLE 1

Figure 4A:
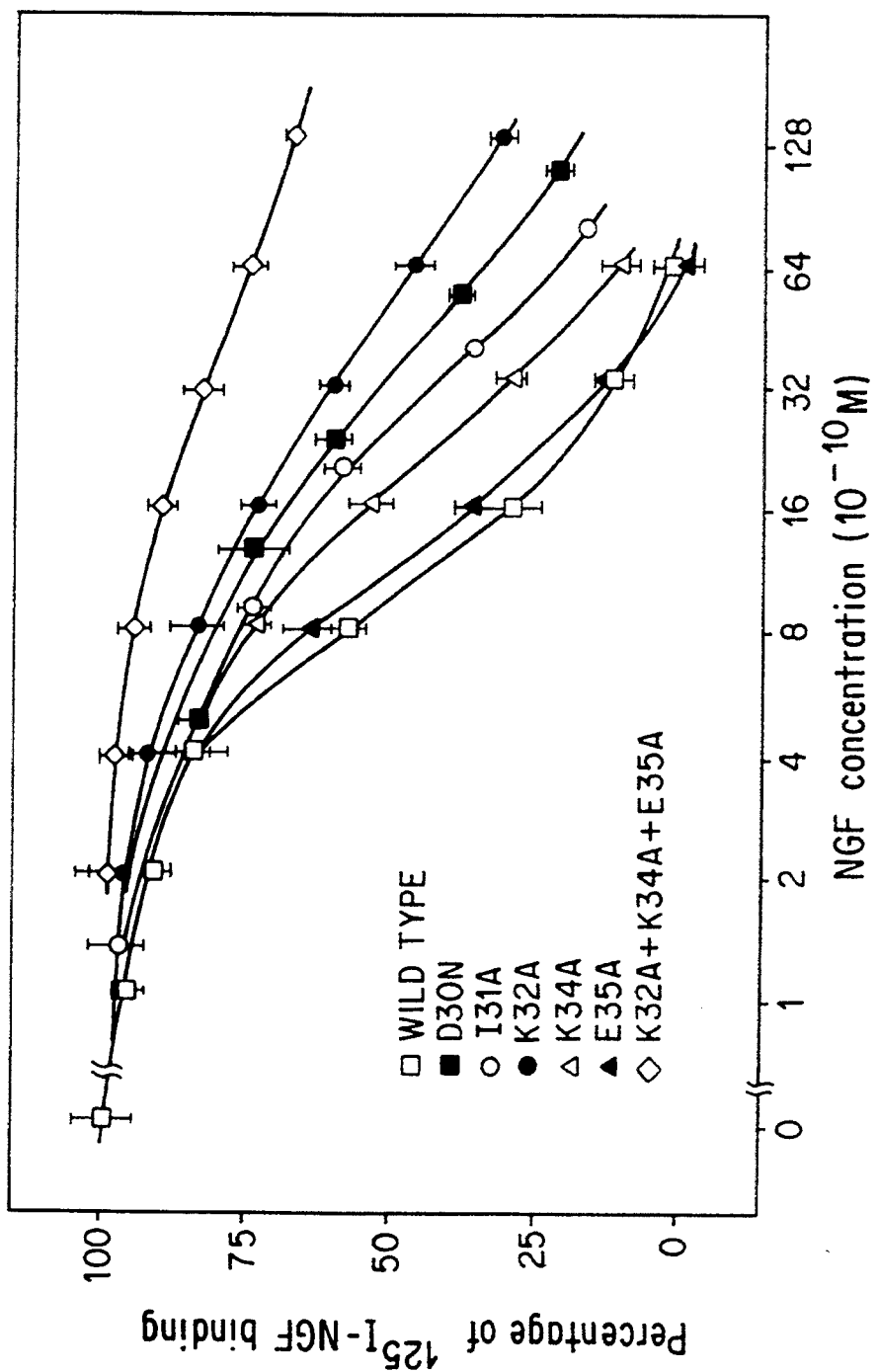

Amino acid residues in the β-hairpin loop 30-34 involved in receptor binding to PC12 cells Experiments and Results Conditioned media containing equal amounts of mutant NGF proteins was used to displace $^{125}$I-NGF from its receptors on the NGF-responsive pheochromocytoma cell line PC12. Competitive binding assays were performed using concentrations of $^{125}$I-NGF (~1.5 nM) at which 80% of the radiolabelled ligand associated with the cells is bound to low-affinity NGF receptors (Sutter et al., 1979). Concentrations of parent and mutant proteins required to displace 50% of the $^{125}$I-NGF from the PC12 cells ($IC_{50}$) were calculated (Table 1). The conservative replacement of Lys25 for Arg or the replacement of either of the three residues (26, 27 and 29) for Ala did not affect the affinity of the protein for receptors on PC12 cells (Table 1). However, a 3 to 4-fold reduction in binding affinity was observed when Asp30 or Ile31 were modified (See Example 2, Table 1, and FIG. 4A). The importance of Ile 31 was further tested by replacement with Met (the residue that occurs at this position in BDNF) (Leibrock et al., 1989) and with Val. Interestingly, only the most conservative change (I31V) allowed a binding affinity similar to parent NGF (Table 1). A marked reduction of receptor binding was seen after replacement of Lys32 with Ala, in which case the affinity was reduced approximately 6-fold compared to parent NGF (Table 1 and FIG. 4A). Replacement of Lys34 with Ala and Val36 with Leu reduced binding to 50 and 45% of the wt, respectively (Table 1 and FIG. 4A). Surprisingly, the incompletely processed E35A mutant showed close to parent binding affinity (Table 1 and FIG. 4A), indicating that intermediates in NGF biosynthesis can bind to NGF receptors as efficiently as the mature protein.

Discussion

Figure 9:
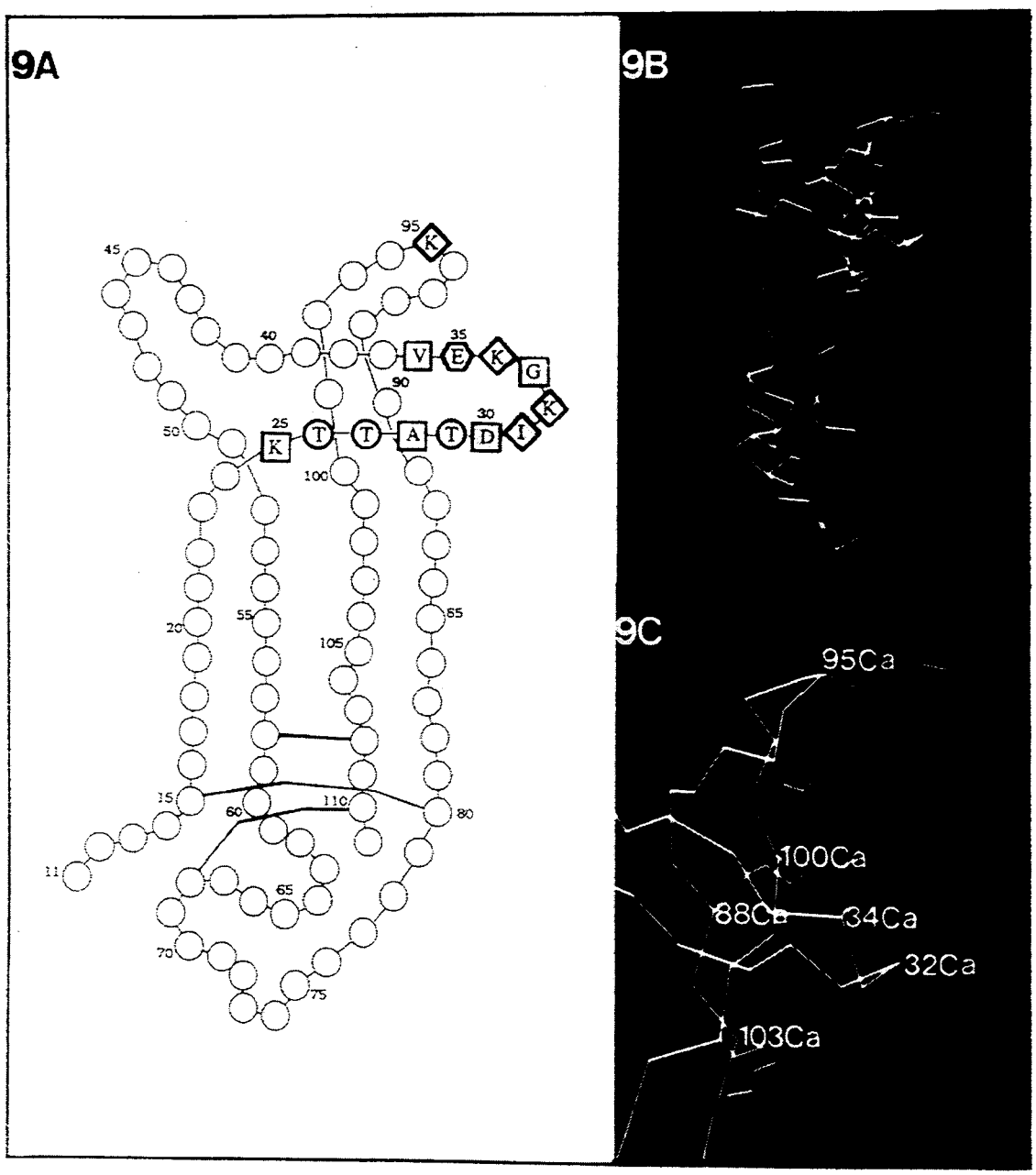

The crystal structure of the NGF dimer (McDonald et al., 1991) reveals a novel structure consisting of three antiparallel pairs of strands and four loop regions which contain almost all the variable residues observed between different NGF-related molecules. One of these loops corresponds to the residues analyzed in the present study and includes a β-hairpin turn (residues 30 to 34). Our results show that residues in region 25-36 are important for stability, receptor binding and biological activity of the NGF molecule (FIG. 9A).

Lys25 was shown to play an important structural role since only the closely related Arg, but not Ala or Gln, could replace Lys at this position to form a stable protein. In agreement with this, the crystal structure revealed that Lys25 makes a side-chain hydrogen bond to Glu55 which is important for the correct folding of the NGF protein (McDonald et al., 1991). Deletion of Ala28 prevented the accumulation of NGF protein in the conditioned media indicating a structural role for this position.

Replacement of Glu 35 for Ala resulted in the production of incompletely processed polypeptides in the range of 23 to 34K which were shown to have similar receptor binding affinity and biological activity as the fully processed, parent molecule. The fact that an in vitro synthesized full-length NGF precursor of 35K was previously shown to have very low levels of biological activity suggests that removal of some amino terminal sequences may be important for the activation of the NGF precursor (Edwards et al., 1988). Our results also demonstrate that, in addition to conserved domains in the NGF propeptide (Suter et al., 1991), residues in the mature molecule also play a role in the biosynthesis of fully processed, mature NGF.

Replacement of the non polar side chain at Val36 with Leu was also shown to affect receptor binding to PC12 cells. In contrast to Ile31, Val36 is deeply buried in the NGF monomer and it appears to be involved in the formation of the hydrophobic core of the NGF subunit (McDonald et al., 1991). The fact that Leu, but not Ala, could replace Val at this position indicates the importance of the hydrophobic contribution of Val36 to the core of the molecule and suggest that the reduced binding of the V36L mutant probably reflects structural rearrangements required to accommodate the larger Leu side-chain at this position.

EXAMPLE 2

Modification of Asp30 and Ile31

Experiments and Results

The specific biological activity of the mutant NGF proteins was first studied by assaying their ability to stimulate neurite outgrowth from E9 chick sympathetic ganglia (Levi-Montalcini and Angeletti, 1968; Ebendal, 1984; Ebendal, 1989). In agreement with their ability to displace $^{125}$I-NGF from PC12 cells, the biological activities of the mutants K25R, T26A, T27A and T29A were all similar to the activity of parent NGF (Table 1). To test the possibility that the Thr residues could compensate for their modification when changed individually, a triple mutant was generated where the three Thr residues were simultaneously replaced by Ala. However, this mutant failed to accumulate in the medium of transfected cells at detectable levels (Table 1).

A 4-fold reduction of biological activity was seen with the D30N and I31A mutants (Table 1 and FIG. 4B) which correlated with their respective receptor binding affinities (Table 1). To eliminate the possibility that the decreased activity was due to the reduced stability of these mutant molecules (FIG. 2C), induction of c-fos mRNA was tested in PC12 cells. It is well documented that maximal induction of c-fos mRNA in these cells takes place within 30–45 min after exposure to NGF (Milbrandt, 1986; Gizango-Ginsberg and Ziff, 1990), a time period that is 20 to 30 times shorter than the estimated half-lives of these molecules. A peak in c-fos mRNA was detected after 30 min exposure of PC12 cells to parent NGF (FIG. 4C). Both the D30N and the I31A mutants induced maximal c-fos mRNA levels after 30 min which, however, were 3–4 fold lower than the maximal level obtained with parent NGF (FIG. 4C).

Interestingly, four mutants with reduced binding affinities to PC12 cells (I31M, K32A, K34A and V36L) showed parent levels of biological activity (Table 1 and FIG. 4B). Thus, for the K32A mutant, the 6-fold reduction in binding did not affect its biological activity in the sympathetic ganglia (compare FIGS. 4A and B). In agreement with the receptor binding data, the E35A mutant displayed parent levels of biological activity, despite the fact that it contained only approximately 5% of a correctly processed, mature protein (Table 1 and FIG. 4B).

Discussion

Several important hydrogen bonding side-chains are buried in the NGF subunit, including Asp30 (McDonald et al., 1991). These results showed that the half life of the NGF molecule is reduced about 20 times when Asp30 is replaced by Ala, a residue that would prevent the proposed hydrogen bond from the sidechain of Asp30 to the main chain at Lys34. The reduced recovery and half-life of the D30N mutant show that Ash can work at this position albeit at a lower efficiency. On the other hand, elimination or alanine replacement of Gly33 resulted in loss of recovery of NGF protein probably due to a reduced stability of the molecule. Glycine at this position allows the formation of a turn by having main-chain torsion angles outside the allowed range for amino acids with a side chain (Sibanda et al., 1989). Taken together, the results with the Asp30 and Gly33 mutants suggest that these residues play a structural role in the stabilization of the $\beta$-hairpin loop 30–34 and that their modification may have functional effects through changes in the conformation of the loop (FIG. 9A). The high conservation of these positions in other members of the NGF family suggest that these residues could play a similar role in the other three neurotrophins.

As a result of the turn at 30 to 34, the hydrophobic Ile31 becomes exposed on the surface of the NGF molecule. Replacement of this residue by Ala reduced both receptor binding in PC12 cells and biological activity. Interestingly, only biological activity but not receptor binding was rescued after replacement into Met, whereas wild type binding and biological activity were seen after change into Val. In addition, preliminary results showed a 5-fold reduction in binding to p140$^{trk}$ in the I31A mutant but parent levels in I31M. Taken together these results suggest a role for the non polar side-chain of Ile31 in both biological activity which correlates with binding to p140$^{trk}$ and low affinity binding (FIG. 9A).

EXAMPLE 3

Simultaneous replacement of Lys32, Lys34 and Glu35 by Ala

Figures 3A, 3B:
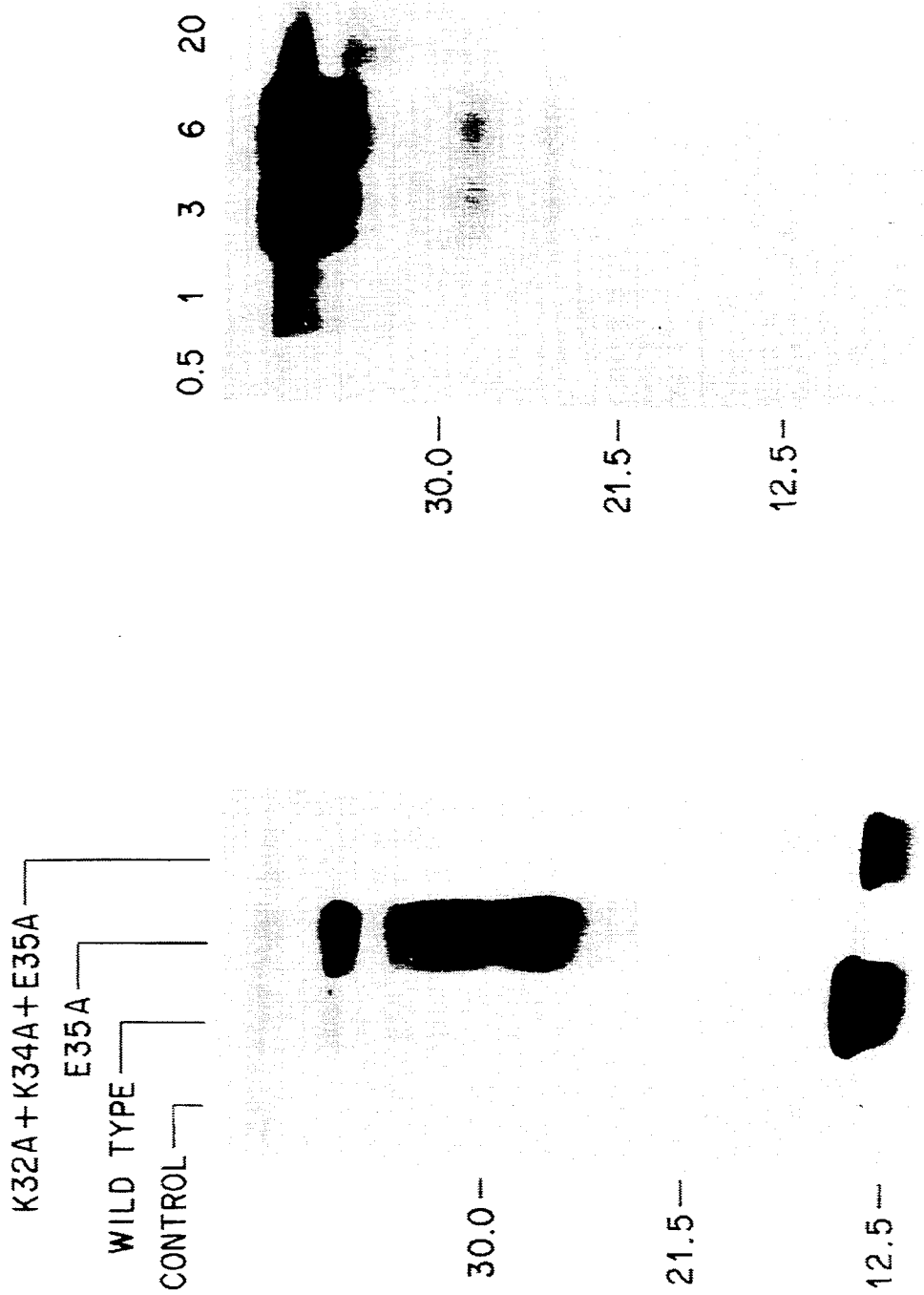
Figure 4B:
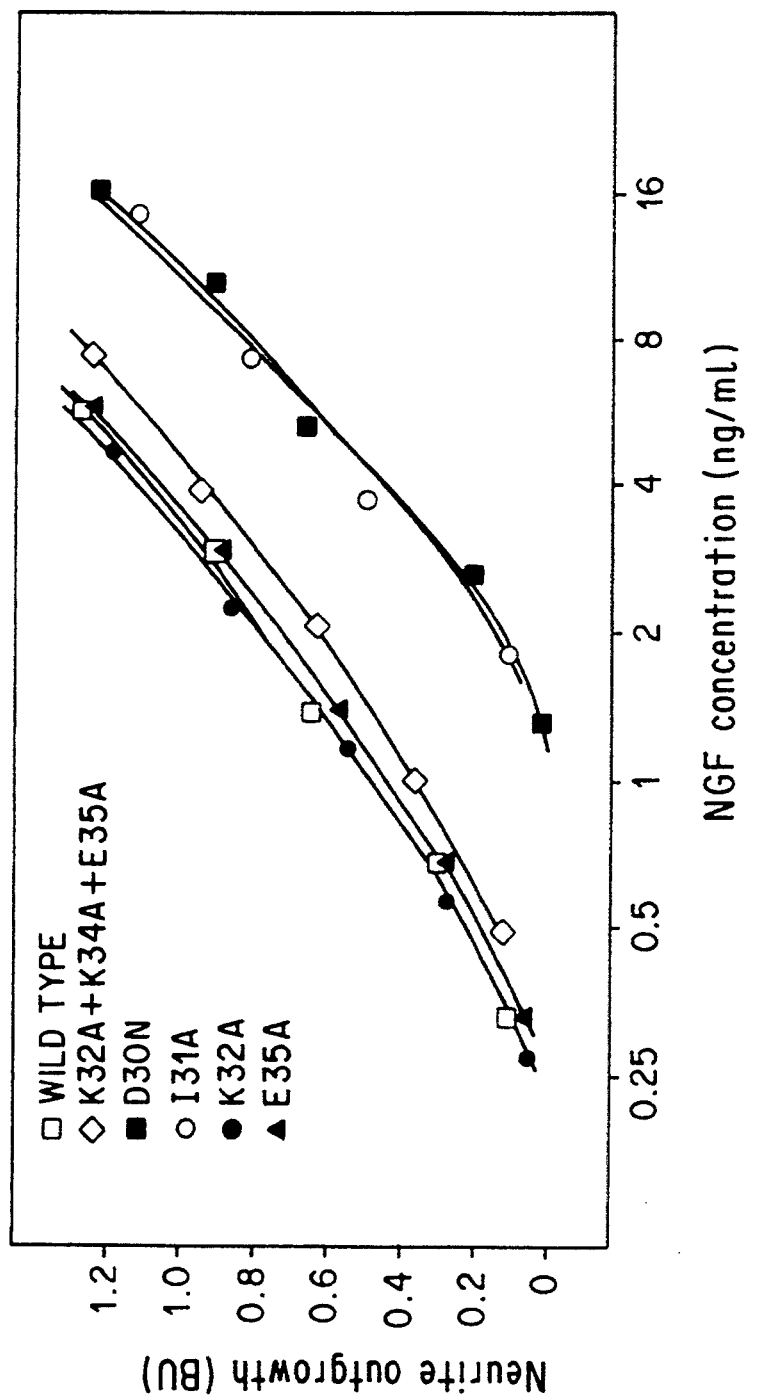
Figure 4C:
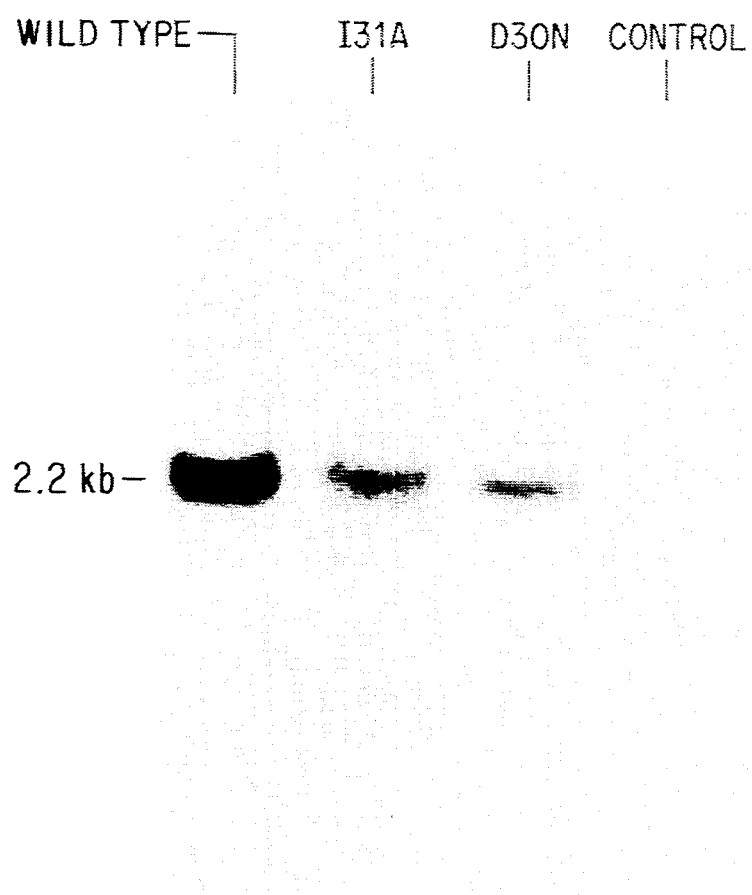

The three charged residues Lys32, Lys34 and Glu35, where an individual mutation had no effect on the biological activity, were simultaneously replaced by Ala, thereby eliminating the charged side chains at these positions. Interestingly, this mutant protein was completely recovered as a fully processed protein in spite of the fact that it contained the E35A mutation (FIG. 3A). The triple mutation reduced binding of this protein to PC12 cells to less than 1% of that seen with the parent molecule (Table 1 and FIG. 4A). The same result was obtained when the cells were preincubated with the mutant protein for 2 hours prior to the addition of $^{125}$I-NGF (not shown). However, the biological activity of the triple mutant in sympathetic ganglia was close to parent NGF activity (Table 1 and FIG. 4B).

Figure 5A:
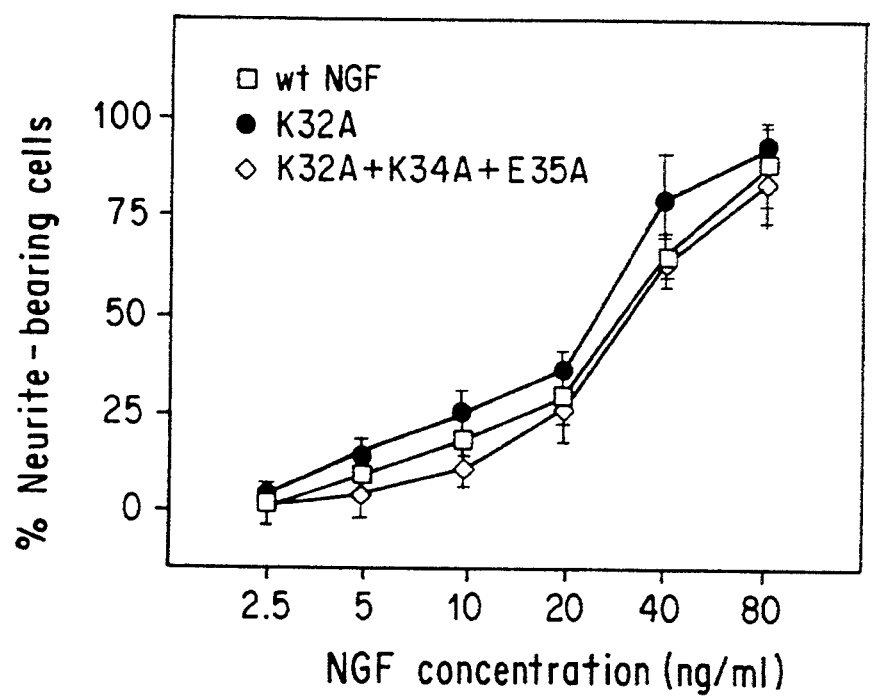

Neurite outgrowth was assayed in PC12 cells to test if the loss of binding correlated with the biological activity in these cells (FIG. 5A). The individual change of Lys32, Lys34 and Glu 35 to Ala did not significantly changed the ability of the proteins to stimulate neurite outgrowth in spite of their different affinities to NGF receptors on these cells. Moreover, the triple mutant (K32A+K34A+E35A) also elicited parent activity despite its greatly reduced low affinity binding to PC12 cells (FIG. 5A).

Figure 5B:
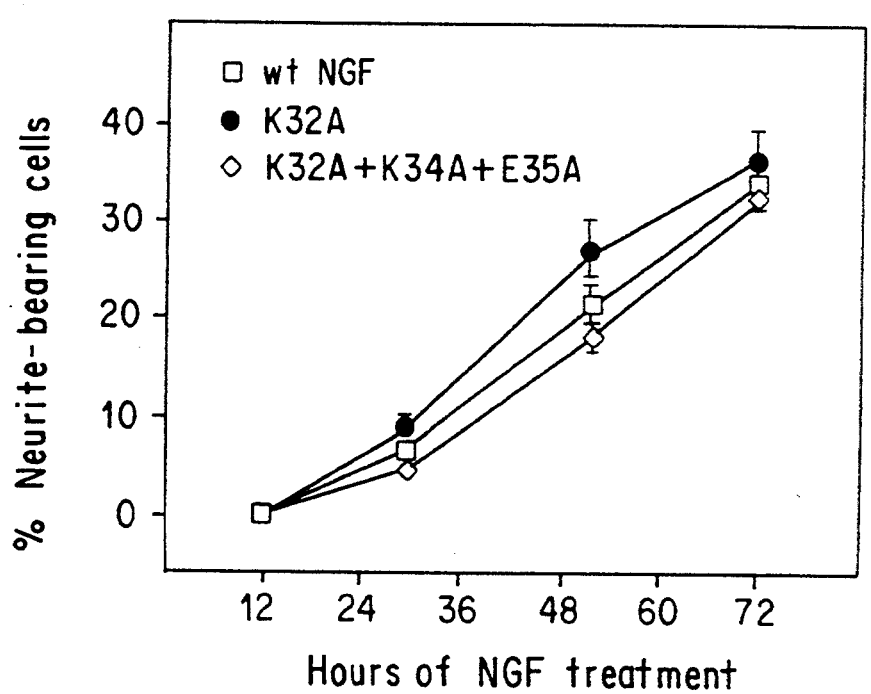
Figure 5C:
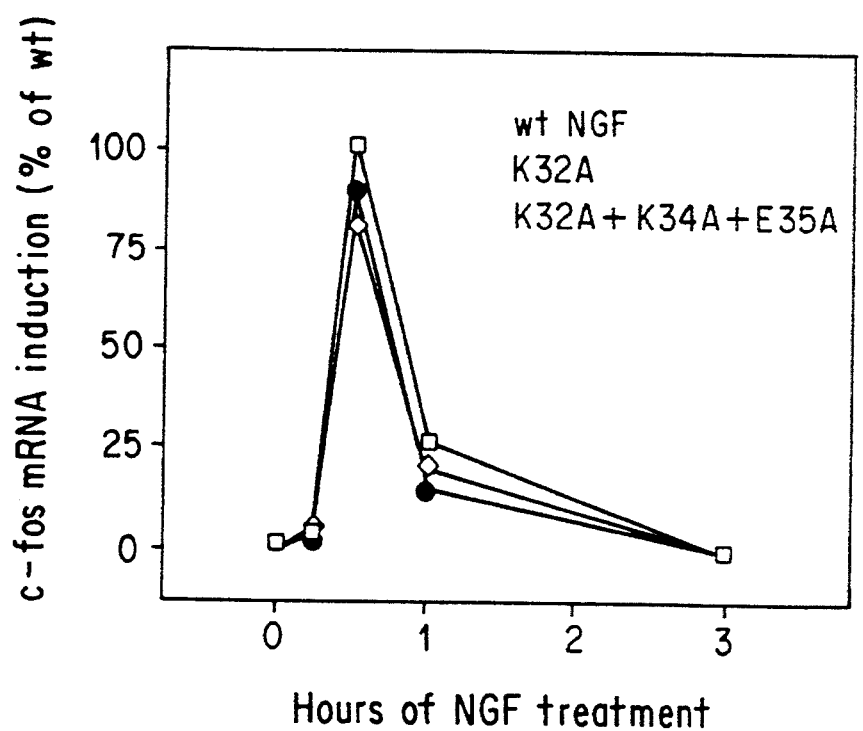

The possibility that the apparent discrepancy observed between binding and biological activity was due to a slower receptor-mediated degradation was also examined. As seen with other peptide hormones which undergo receptor mediated endocytosis (i.e. insulin), a reduced binding affinity may not always translate into a reduced biological activity when examined over a longer period of time. As a consequence of the reduced binding, mutant molecules may have a lower rate of receptor-mediated degradation which results in a slower but prolonged biological activity that can reach parent levels when integrated over a period of time. To investigate this possibility, the kinetics of both an early (c-fos mRNA induction) and a delayed (stimulation of neurite outgrowth) response in PC12 cells were studied. Despite their reduced binding affinities, both the K32A and the triple mutant induced c-fos mRNA and neurite outgrowth with the same time course and intensity as the parent molecule (FIGS. 5B and C).

EXAMPLE 4

Affect of Mutation of Lys32 and Lys34 on NGF binding

Receptor binding assays to PC12 cells were performed using high concentrations of $^{125}$I-NGF at which most of the observed binding is of the low-affinity type (Sutter et al., 1979). However, since PC12 cells express both p75$^{NGFR}$ and p140$^{trk}$ receptors (Herrup and Thoenen, 1979; Hosang and Shooter, 1985; Kaplan et at., 1991b) these results can not clearly discriminate between the binding of the mutant NGFs to either one of these two molecules. Therefore, the binding affinities were compared of the mutants K32A, K34A, E35A and the triple mutant K32A+K34A+E35A to A875 cells, a human melanoma cell line which expresses high amounts of only p75$^{NGFR}$ (Buxser et al., 1983) and to rtrk-3T3 cells, a fibroblast cell line that expresses only rat p140$^{trk}$ (Kaplan et al., 1991a).

Figure 6A:
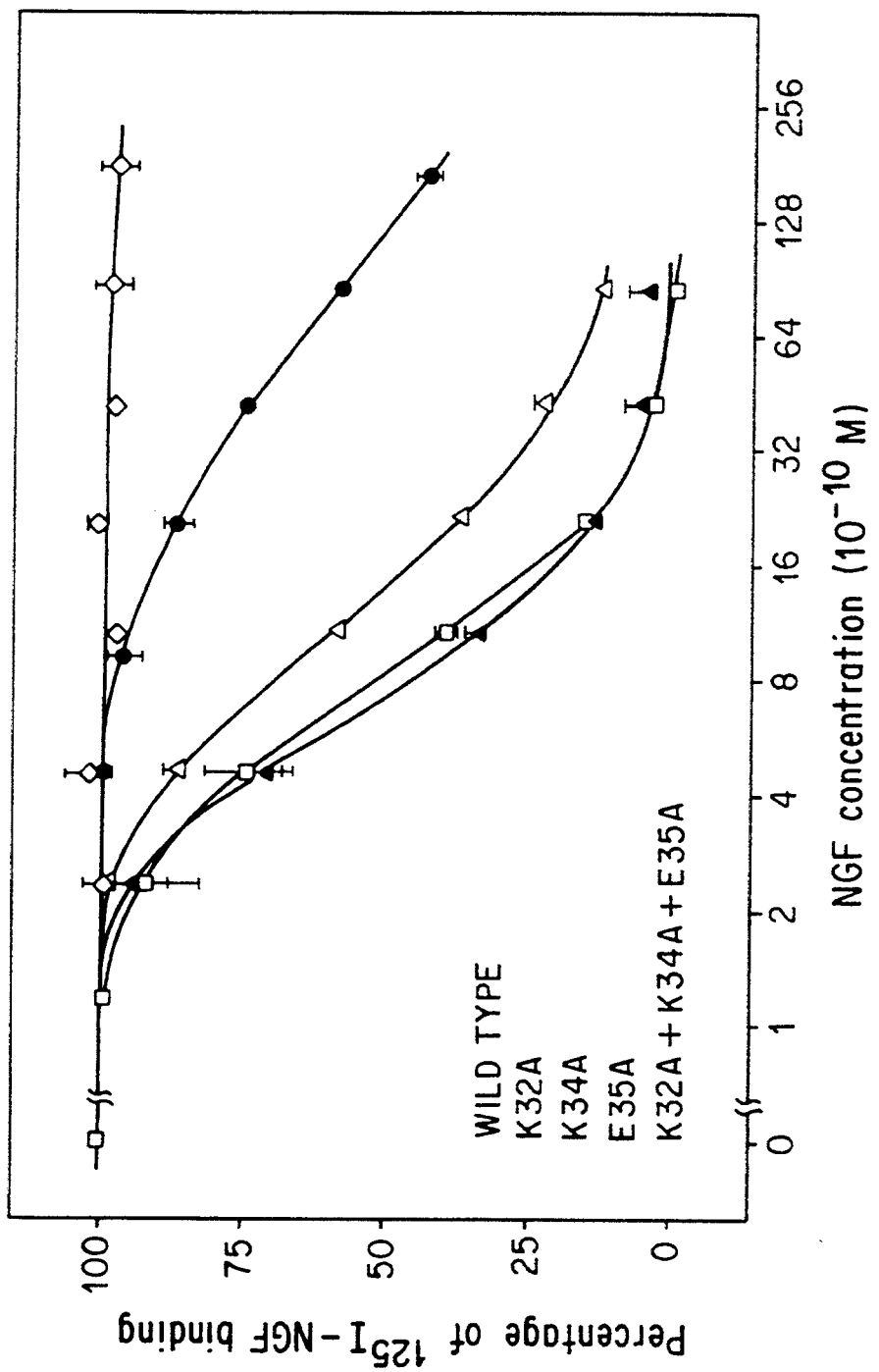
Figure 6B:
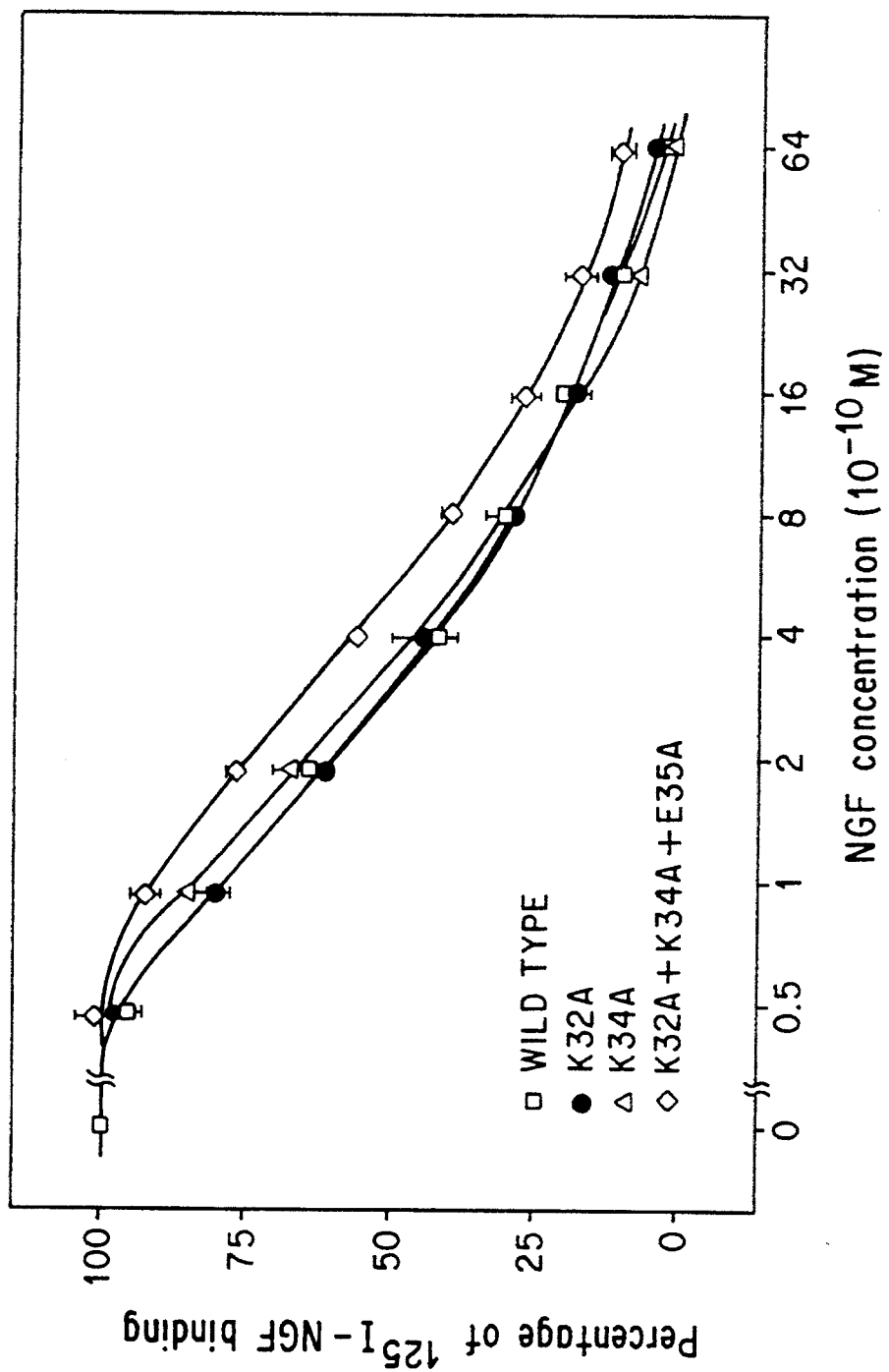

The replacement of the positively charged side chain of Lys32 by the methyl group of Ala reduced the binding of the molecule to p75$^{NGFR}$ to 5% of the binding seen with parent NGF (Table 2 and FIG. 6). The change of Lys34 into Ala reduced binding to A875 cells to 55% of the parent levels. However, the simultaneous replacement of Lys32, Lys34 and Glu35 completely abolished the binding of the mutant molecule to p75$^{NGFR}$ (Table 2 and FIG. 6). The individual change of Glu35 into Ala had no effect on the binding affinity to A875 cells (Table 2 and FIG. 6), indicating that the loss of binding seen with the triple mutant was due to the modification of the positively charged residues Lys32 and Lys34.

Despite its 20-fold reduction in binding to p75$^{NGFR}$, the K32A mutant was indistinguishable from parent NGF in binding to p140$^{trk}$ expressed on rtrk-3T3 cells (Table 2 and FIG. 6). Similarly, also the K34A and E35A mutants showed parent affinity to p140$^{trk}$ (Table 2 and FIG. 6). Interestingly, the triple mutant, which failed to displace $^{125}$I-NGF from p75$^{NGFR}$, retained significant binding to p140$^{trk}$, at about 55% of the level seen with parent NGF (Table 2 and FIG. 6). Furthermore, in an additional embodiment involving the NGF molecule, Lys32, Lys34 and Lys95 form a positively charged interface involved in binding to p75$^{NGFR}$. Simultaneous modification of Lys32 with either of the two other lysines results in loss of binding to p75$^{NGFR}$. Despite the lack of binding to p75$^{NGFR}$, these mutants retain binding to p140$^{trk}$ as well as biological activity, as measured by neuronal differentiation of PC12 cells and survival of cultured sympathetic neurons.

EXAMPLE 5

Modification of residues in the 25–36 region alters the stability of the NGF molecule.

Alanine-scanning mutagenesis (Cunningham and Wells, 1989) was applied to map structurally and functionally important residues in the region between amino acid residues 25 and 36 of rat NGF. This region is highly conserved among different species of vertebrates (FIG. 1A) and shows 50–60% conservation in other members of the NGF family (FIG. 1B). Mutant proteins were transiently expressed in COS cells. The yield of mutant protein production was assessed by SDS-PAGE of metabolically labeled polypeptides in conditioned media of transfected cells in order to standardize for the amount of mutant protein used for receptor binding and biological assays. As shown in Table 1, the levels of mutant NGF proteins varied over a 10-fold range. Five of the mutant NGF proteins (K25A, A28Δ, D30A, G33Δ and V36A) did not accumulate in the medium at detectable levels. Interestingly, these residues correspond to the five positions from this domain that are strictly conserved among the different members of the NGF family (FIG. 1B). No protein was detected either after Lys25 or Gly 33 were changed into the more similar amino acid residues Gln and Ala, respectively (Table 1). In contrast, the D30A and V36A mutants could be rescued by replacement into Asn and Leu, respectively, though at lower levels than those seen with the wild type (wt) protein (Table 1). Lys25 was also changed into Arg, the most conservative replacement possible at this position. This mutation allowed the detection of NGF protein at about 50% of the levels of the parent protein (Table 1).

Figure 2B:
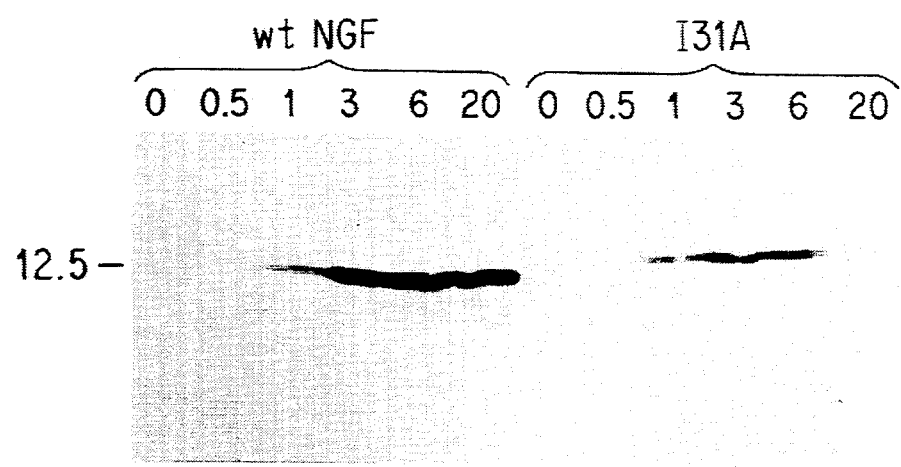
Figure 2C:
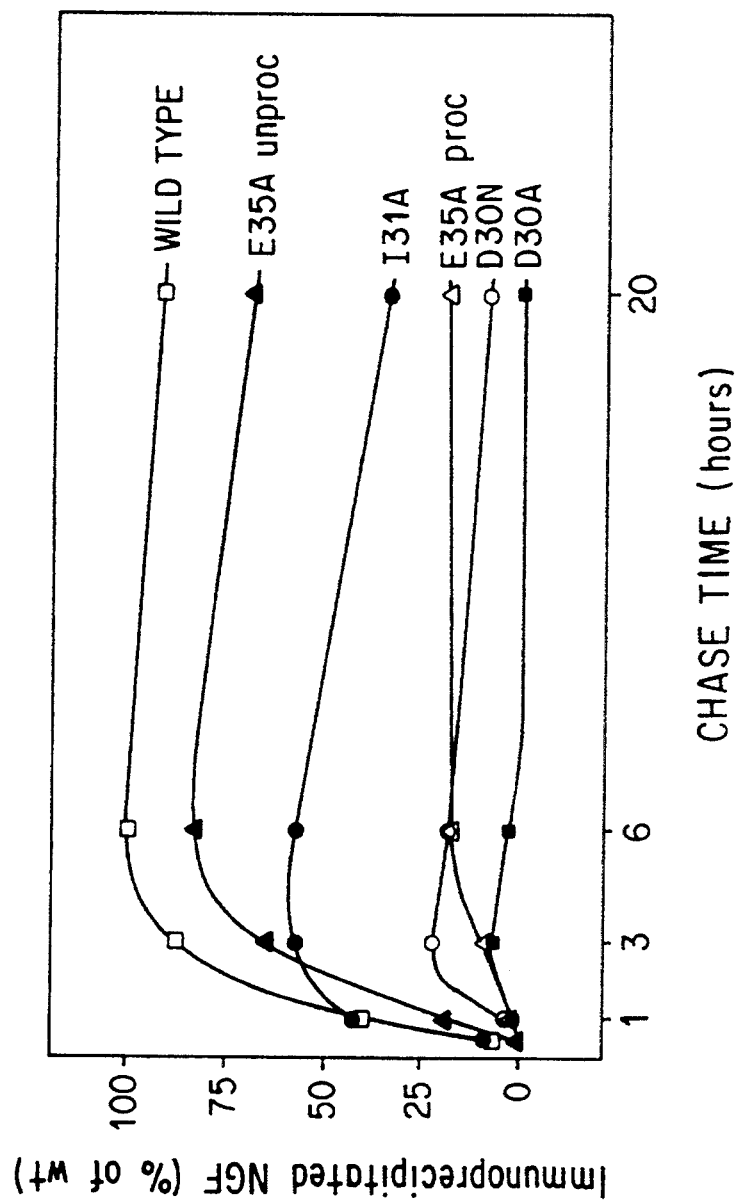

The variations observed in the amounts of mutant protein may reflect differences in protein synthesis, stability or secretion of individual polypeptides in COS cells. To discriminate between these possibilities, pulse-chase experiments were carried out followed by immunoprecipitation and SDS-PAGE. After a 15 min pulse, a predominating 23K parent NGF precursor protein could be immunoprecipitated from cellular extracts (FIG. 2A). Fully processed, mature 13K NGF was detected after 30 min of chase and almost all of the intracellular NGF disappeared after three hours. The disappearance of intracellular NGF correlated with the appearance of NGF in the media which peaked 6 hours after the chase and remained at this level for at least 14 more hours (FIG. 2B). The I31A mutant, which was produced 3 to 4 times lower than parent NGF (Table 1), accumulated in the transfected cells to a similar extent as the parent protein (FIG. 2A). However, lower levels of the I31A mutant were detected in the media, and a drop of 50% was seen in the last 17 hours after the chase (FIG. 2B), indicating a reduced stability of the I31A protein. Similarly, the amount of the D30N mutant protein, produced at 10-fold lower levels than parent NGF (Table 1), decreased significantly after 3 hours of chase (FIG. 2C). In addition, very low levels of the D30A mutant protein could be seen after 3 hours of chase, although they dropped to undetectable levels in the following 12 hours (FIG. 2C). The reduced half-lives of the I31A, D30N and D30A mutant proteins, estimated to be 18, 12 and 3 hours, respectively, indicated that the reduced yields of these mutants were due to lower stability of these proteins in the conditioned media. The greatly reduced peak levels seen after 3 hours of chase in the D30N and D30A mutants suggested that in this case protein synthesis could also be affected (FIG. 2C).

EXAMPLE 6

Replacement of Glu 35 for Ala

Fully processed, mature E35A mutant protein was detected in the conditioned media at a level corresponding to 5% of parent NGF (Table 1). However, after immunoprecipitation, several higher molecular weight polypeptides (in the range of 23 to 34K) were seen which were only very weakly detected in the parent NGF sample (FIG. 3A). Pretreatment of the conditioned media at 70° C. in the presence of 1% SDS and 1.5M NaCl prior to immunoprecipitation did not affect the polypeptide pattern immunoprecipitated from the E35A mutant (not shown), indicating that the higher molecular weight polypeptides did not represent unrelated proteins that coprecipitated with the E35A mutant. Instead, the size of these polypeptides suggests that they represent incompletely processed intermediates in the biosynthesis of the E35A protein. Pulse-chase experiments using this mutant revealed that both the incompletely processed and mature forms of this protein were very stable in the conditioned media (FIGS. 2C and 3B).

EXAMPLE 7

Effect of Alterations in Lys95 on $p75^{NGFR}$ binding

Experiments and Results

Figure 7A:
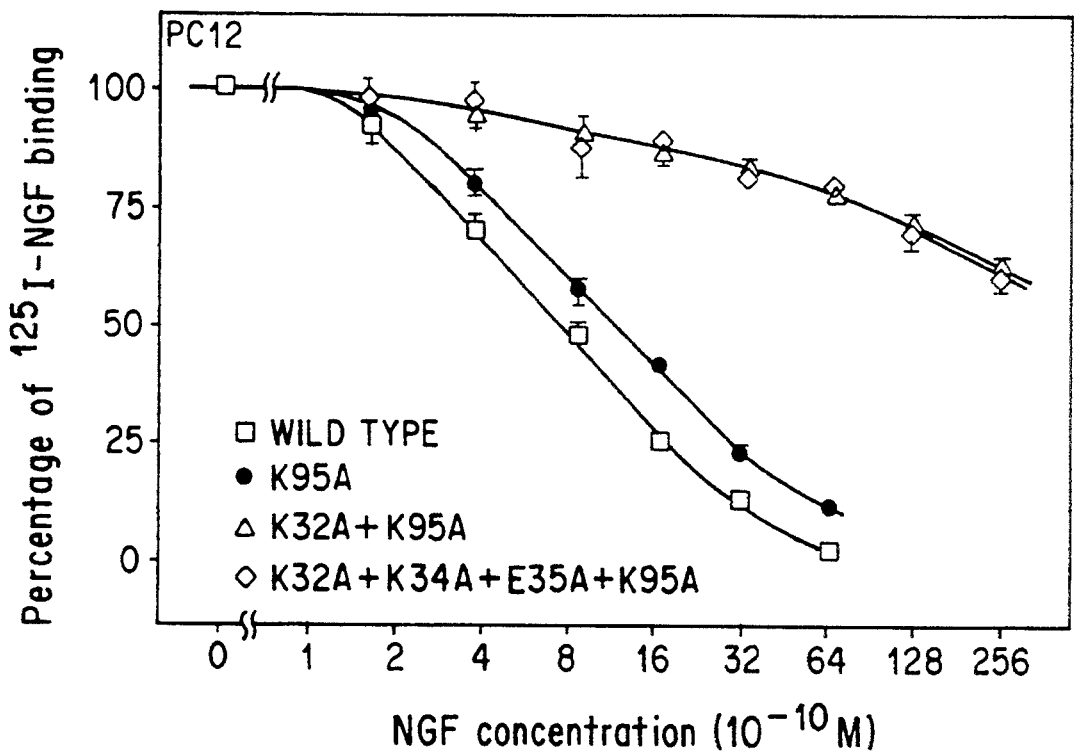
Figure 7B:
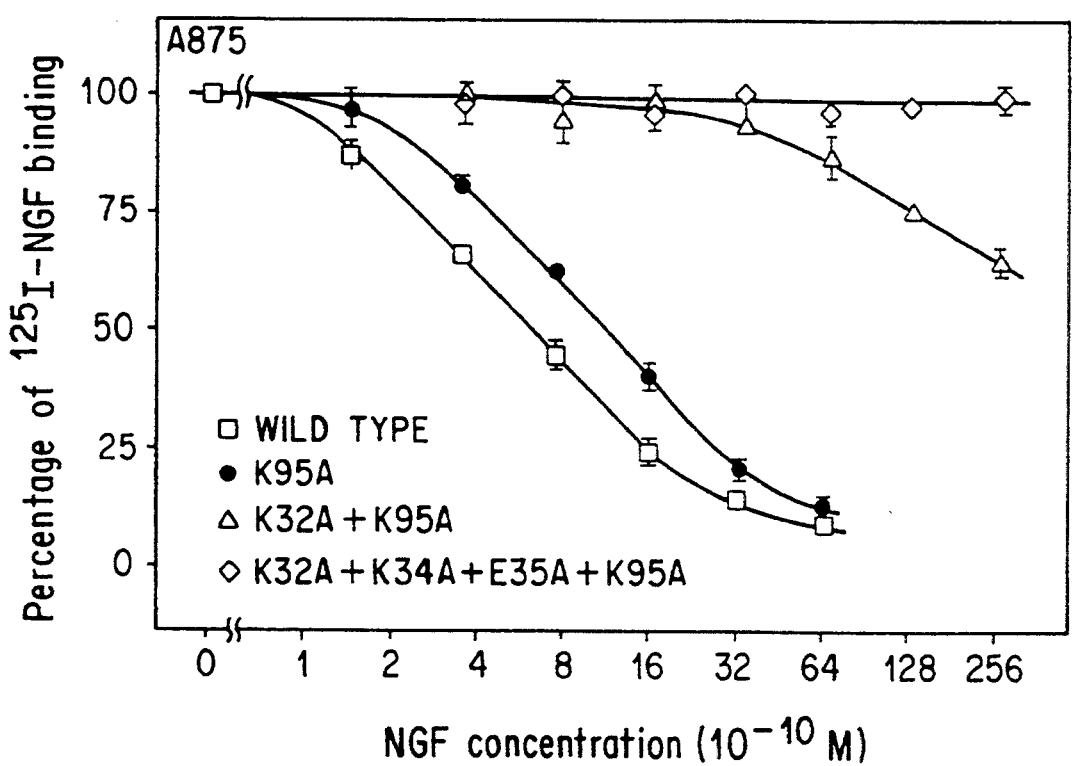
Figure 7C:
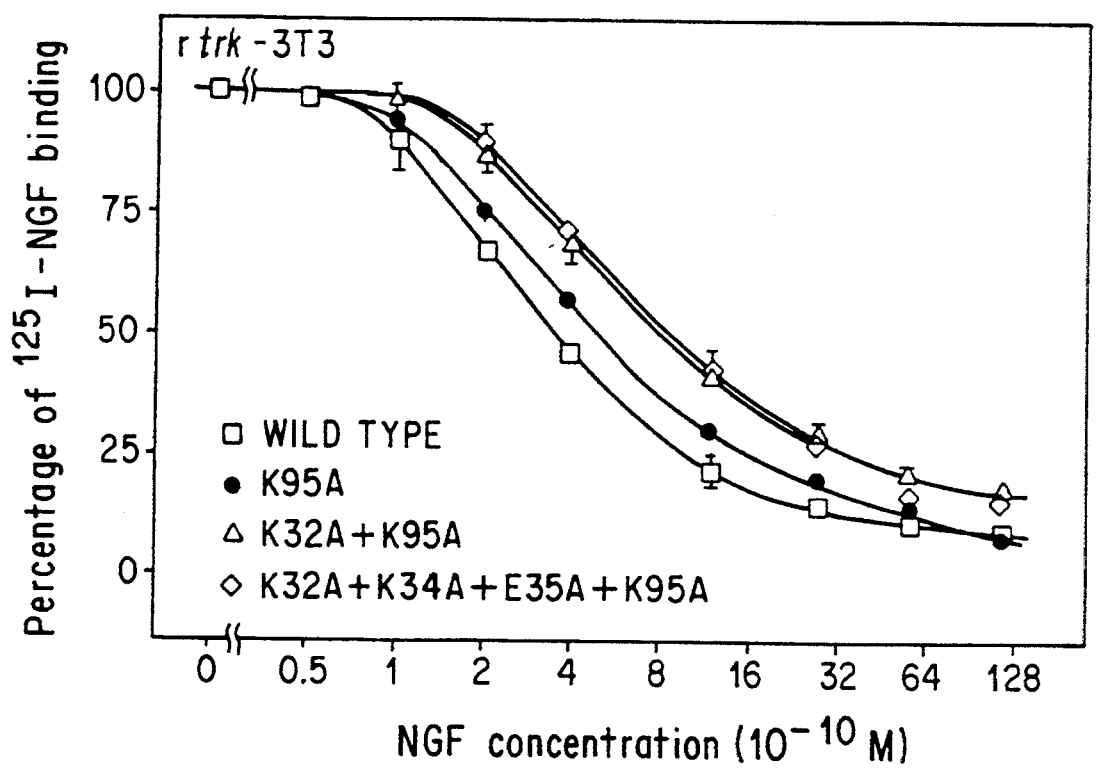
Figure 8A:
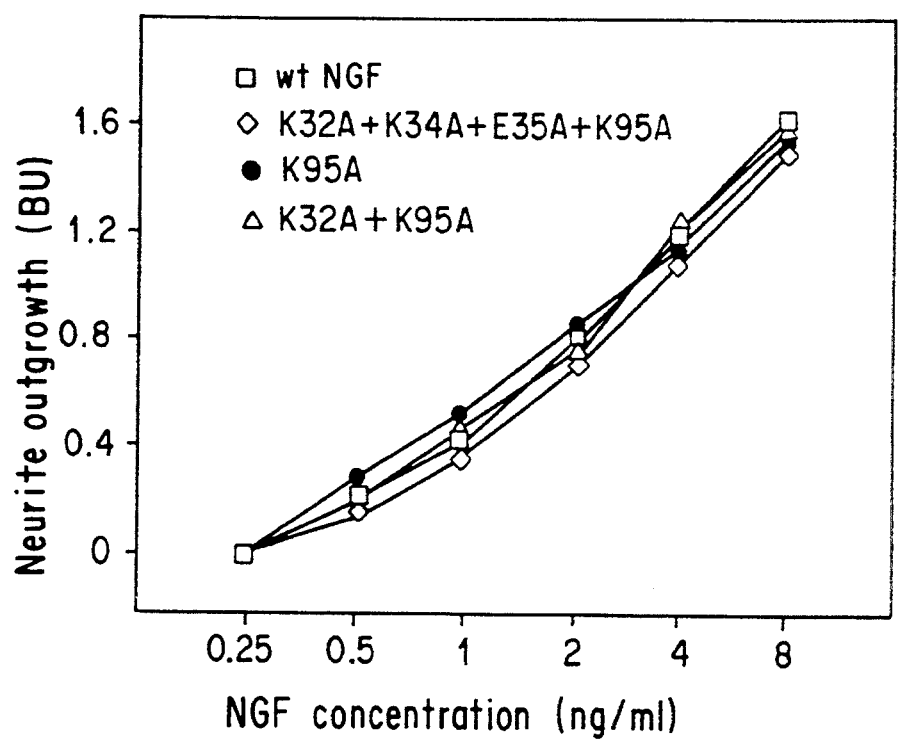

The results with the Lys32, Lys34 and the triple mutant suggest that these two positively charged residues form contact points between NGF and the $p75^{NGFR}$ molecule. Examination of the NGF crystal structure with computer graphics revealed that another positively charged residue, Lys95, is spatially close to Lys32 and Lys34. As in the case of the other two residues, Lys95 is also fully exposed and does not participate in secondary interactions. To test the possibility that Lys95 could also take part in the contact to the $p75^{NGFR}$ molecule, this residue was replaced by Ala. A double mutant K32A+K95A and a quadruple mutant K32A+K34A+E35A+K95A were also generated. The K95A mutant showed 65% binding to PC12 cells compared to parent NGF (FIG. 7). However, combination of K95A with K32A or with K32A+K-34A+E35A drastically reduced binding to PC12 cells to 0.7% of parent levels (FIG. 7). The reduction of low-affinity binding to PC12 cells correlated with loss of binding to $p75^{NGFR}$ expressed on A875 cells (Table 2 and FIG. 7). In the case of the quadruple mutant, no $IC_{50}$ could be calculated. However, despite their inability to bind to $p75^{NGFR}$, these mutants retained the ability to displace $^{125}I$-NGF from $p140^{trk}$ expressed on fibroblasts (Table 2 and FIG. 7) and promoted neurite outgrowth from sympathetic neurons (FIG. 8A) at significant levels.

Figure 8B:
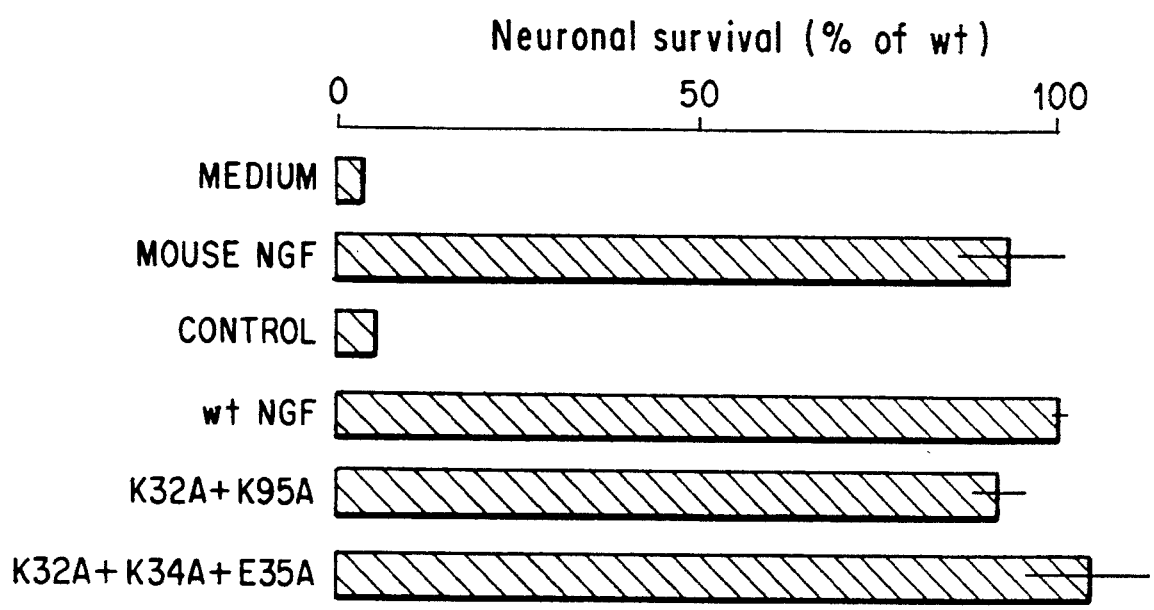

The triple mutant K32A+K34A+E35A and the double mutant K32A+K95A offer a possibility to examine the role of $p75^{NGFR}$ in neuronal survival. Dissociated sympathetic neurons from the rat superior cervical ganglion were tested for survival after 3 days in culture. Less than 5% of the cells survived in the presence of media from mock transfected cells or in normal media when compared to parent NGF or purified mouse NGF (FIG. 8B). However, in cultures treated with the mutant NGFs the extent of neuronal survival was identical to what was seen with the parent protein (FIG. 8B).

Discussion

The crystal structure of NGF revealed a cluster of exposed positively charged side chains close to and around the β-hairpin loop 30–34 (FIGS. 9B and C) (McDonald et al., 1991). It is possible that the high overall negative charge observed for the $p75^{NGFR}$ (an estimated pI of 4.4 (Radeke et al., 1987) may require a complementary ionic interaction from the highly basic NGF dimer (pI 9.3) in this region. The results presented here provide strong support to the notion that these positively charged amino acid residues serve as the main points of contact between NGF and $p75^{NGFR}$. Several lines of evidence support this hypothesis: First, as revealed by the crystal structure, Lys32, Lys34 and Lys95 are highly exposed (50–70% side-chain solvent accessibility) and their side-chains do not have a structural role in the molecule (McDonald et al., 1991). Second, as shown here, replacement of Lys32 for Ala reduced by 6-fold the affinity of the mutant to receptors on PC1'2 cells under low-affinity binding conditions. Third, the simultaneous replacement of Lys32, Lys34 and Glu 35 further reduced low affinity binding to PC12 cells to less than 1% of that seen with parent NGF. This was not due to the E35A mutation since replacement of Glu35 for Ala did not change the affinity of binding. Fourth, replacement of Lys95 had a synergistic effect when combined with K32A, reducing the binding to PC12 cells to almost undetectable levels. Fifth, in all cases, the loss of low-affinity binding to PC12 cells correlated with loss of binding to p75$^{NGFR}$ expressed on A875 cells. In the case of the triple mutant K32A+K34A+E35A and the double mutant K32A+K95A binding to p75$^{NGFR}$ was completely abolished or reduced 150-fold, respectively. And sixth, despite the loss of binding to p75$^{NGFR}$, all mutant NGFs retained binding to p140trk and biological activity, further demonstrating that the loss of low-affinity binding was not due to drastic alterations in conformation of the mutant proteins.

The synergistic effects observed with the multiple lysine mutants indicate that these positively p75$^{NGFR}$ residues cooperate in the formation of an interface for binding to p75$^{NGFR}$ (FIGS. 9B and C). Lys32 appears to be making the strongest contact followed by Lys34 and Lys95 which are probably responsible for the residual binding observed in the K32A mutant. Additional positively charged residues, like the previously studied Arg100 and Arg103 (Ibànez et al., 1990) and perhaps Lys88, may also contribute to the binding interface (FIGS. 9B and C). The loss of binding to p75$^{NGFR}$ in the K32A+K34A+E35A and the K32A+K95A mutants suggests that a minimal number of positive charges are required on the surface of the NGF molecule to provide a stable contact with p75$^{NGFR}$. This model does not rule out the possibility that other type of contacts like, for example, the hydrophobic residue Ile31, may also contribute to stabilize the association between NGF and p75$^{NGFR}$.

The other three known neurotrophins can also bind to the low-affinity NGF receptor (Rodriguez-Tébar et al., 1990; Ernfors et al., 1990; Squinto et al., 1991; Hallböök et al., 1991). Lys95 is conserved in all four proteins described so far and, in NT-3 and NT4, Lys32 is replaced by Arg, another positively charged amino acid residue. Lys34 is also conserved in NT-4. However, in BDNF, Lys32 and Lys34 are replaced by Ser and Gly, respectively. Interestingly, the spatially close loop of residues 93 to 96 in BDNF has three consecutive positively charged residues that may compensate for the absence of Lys32 and Lys34. In support for this hypothesis, a chimeric NGF molecule which has residues 23 to 35 (variable region I) replaced by the corresponding residues in BDNF (Ibànez et al., 1991a) showed a 10-fold reduction of low affinity binding to PC12 cells. The low affinity binding was restored in another chimeric molecule that contains both variable region I and residues 94 to 98 (variable region V) from BDNF, indicating that the three positively charged residues at positions 95, 96 and 97 in BDNF can indeed compensate for the lack of Lys32 and Lys34. Although both NGF and BDNF appear to equally compete for binding to p75$^{NGFR}$, this receptor also recognizes differences between the two ligands which are reflected, in the case of BDNF, by positive cooperativity and slower dissociation kinetics (Rodriguez-Tébar et al., 1990). It therefore appears that BDNF and NGF are recognized by p75$^{NGFR}$ as similar albeit not identical structures. These results offer a structural explanation for the observed differences between NGF and BDNF and suggest that other neurotrophins may interact with p75$^{NGFR}$ through the same region.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

TABLE 1

Relative yield, receptor binding to PC12 cells and specific biological activity of wild type and mutant NGF proteins

| Mutant Protein[a] | Yield[b] | Receptor Binding[c] % of wild type | Biological Activity[c] |
|---|---|---|---|
| wild type | 100 | 100 | 100 |
| K25A | — | — | — |
| K25Q | — | — | — |
| K25R | 50 | 130 | 100 |
| T26A | 40 | 100 | 100 |
| T27A | 46 | 120 | 63 |
| A28Δ | — | — | — |
| T29A | 18 | 71 | 74 |
| T26A + T27A + T29A | — | — | — |
| D30A | — | — | — |
| D30N | 11 | 25 | 23 |
| I31A | 28 | 30 | 25 |
| I31M | 50 | 35 | 100 |
| I31V | 34 | 130 | 100 |
| K32A | 76 | 16 | 100 |
| G33Δ | — | — | — |
| G33A | — | — | — |
| K34A | 53 | 50 | 100 |
| E35A | 5[d] | 85[e] | 85[e] |
| K32A + K34A + E35A | 65 | <1 | 65 |
| V36A | — | — | — |
| V36L | 51 | 33 | 90 |

[a]Mutants are abbreviated by the wild type (wt) residue (single amino acid designation), followed by its codon number and the mutant residue. Δ indicates that the corresponding residue was deleted.
[b]Steady-state levels calculated after SDS-PAGE of metabolically labeled conditioned media. The short line indicates that the level of mutant protein was below detection (<2% of wt NGF).
[c]Data from two dose-response experiments varied by ±10% of the average values reported here.
[d]Data based on the fully processed form (see text for details).
[e]Data based on both processed and unprocessed forms (see text for details).

TABLE 2

Relative receptor binding to A875 cells and rtrk-NIH3T3 cells of wild type and mutant NGF proteins.

| Mutant Protein | binding to A875 cells | binding to rtrk-NIH3T3 cells |
|---|---|---|
| | % of wild type | |
| wild type | 100 | 100 |
| K32A | 5 | 100 |
| K34A | 5 | 90 |
| E35A | 100 | 100 |
| K32A + K34A + E35A | no IC$_{50}$ | 55 |
| K95A | 55 | 80 |
| K32A + K95A | <A | 40 |
| K32A + K34A + E35A + K95A | no IC$_{50}$ | 40 |

Data from three independent experiments varied by ±10% of the average values reported here.

REFERENCES

Angeletti, R. H. and Bradshaw, R. A. (1971). Nerve growth factor from mouse submaxillary gland: amino acid sequence. Proc. Natl. Acad. Sci. USA 68, 2417–20.

Angeletti, R. H., Hermodson, M. A. and Bradshaw, R. A. (1973). Amino acid sequences of 2.5S nerve growth factor. II Isolation and characterization of the thermolytic and peptic peptides and the complete covalent structure. Biochemistry 12, 100–15.

Banerjee, S. P., Snyder, S. H., Cuatrecasas, P. and Greene, L. A. (1973). Binding of nerve growth factor in superior cervical ganglia. Proc. Natl. Acad. Sci. USA 79, 2519-2523.

Barde, Y. -A., Edgar, D. and Thoenen, H. (1982). Purification of a new neurotrophic factor from mammalian brain. Embo J. 1, 549-553.

Berg, M., Sternberg, D., Hempstead, B. and Chao, M. (1991). The low-affinity p75 nerve growth factor (NGF) receptor mediates NGF-induced tyrosine phosphorylation. Proc. Natl. Acad. Sci. USA 88, 7106-7110.

Buxser, S. E., Watson, L., Kelleher, D. J. and Johnson, G. L. (1983). Purification of the receptor for nerve growth factor from A875 melanoma cells by affinity chromatography. J Biol Chem 258, 3370-5.

Cordon-Cardo, C., Tapley, P., Jing, S., Nanduri, V., O'Rourke, E., Lambelle, F., Kovary, K., Klein, R., Jones, K., Reichardt, L. and Barbacid, M. (1991). The trk tyrosine kinase mediates the mitogenic properties of nerve growth factor and neurotrophin-3. Cell 66, 173-183.

Cunningham, B. C. and Wells, J. A. (1989). High-resolution epitope mapping of hGH-receptor interactions by alanine-scanning mutagenesis. Science 244, 10811085.

Curran, T., Gordon, M. B., Rubino, K. L. and Sambucetti, L. C. (1987) Isolation and characterization of the c-fos (rat) cDNA and analysis of post-translational modification in vitro. Oncogene 2, 79-84.

Ebendal, T. (1984). In Organizing Principles of Neural Development, S. Sharma, eds. (New York: Plenum Press), pp. 93-107.

Ebendal, T. (1989). Use of collagen gels to bioassay nerve growth factor activity. In Nerve Growth Factors, R. A. Rush, eds. (Chichester: John Wiley & Sons), pp. 81-2 4

Ebendal, T., Larhammar, D. and Persson, H. (1986). Structure and expression of the chicken~nerve growth factor. EMBO J. 5, 1483-7.

Ebendal, T., Persson, H., Larhammar, D., Lundstromer, K. and Olson, L. (1989). Characterization of antibodies to synthetic nerve growth factor (NGF) and proNGF peptides. J Neurosci Res 22, 223-240.

Edwards, R. H., Selby, M. J., Garcia, P. D. and Rutter, W. J. (1988). Processing of the native nerve growth factor precursor to form biologically active nerve growth factor. J. Biol. Chem. 263, 6810-5.

Ernfors, P., Hallböök, F., Ebendal, T., Shooter, E., Radeke, M. J., Misko, T. P. and Persson, H. (1988). Developmental and regional expression of~-Nerve Growth Factor receptor mRNA in the chick and rat. Neuron 1, 983-996.

Ernfors, P., Ibariez, C. F., Ebendal, T., Olson, L. and Persson, H. (1990). Molecular cloning and neurotrophic activities of a protein with structural similarities to~-nerve growth factor: developmental and topographical expression in the brain. Proc. Natl. Acad. Sci. USA 87, 5454-5458.

Gizang-Ginsberg, E. and Ziff, E. (1990). Nerve growth factor regulates tyrosine hydroxylase gene transcription through a nucleoprotein complex that contains c-Fos. Genes Dev 4, 477-491.

Greene, L .A. and Tischler, A. S. (1976). Establishment of a noradrenergic clonal line of rat adrenal pheochromocytoma cells which respond to nerve growth factor. Proc. Natl. Acad. Sci. USA 73, 2424-8.

Hallöök, F., Ayer.LeLievre, C., Ebendal, T. and Persson, H. (1990). Expression of nerve growth factor receptor mRNA during early development of the chicken embryo: emphasis on cranial ganglia. Development 10~, 693-704.

Hallböök, F., Ibanez, C. F. and Persson, H. (1991). Evolutionary studies of the nerve growth factor family reveal a novel member abundantly expressed in Xenopus ovary. Neuron 6, 845-858.

Hempstead, B., Martin-ZAnca, D., Kaplan, D., Parada, L. and Chao, M. (1991). High-affinity NGF binding requires coexpression of the trk proto-oncogene an~1 the low-affinity NGF receptor. Nature 350, 678-683.

Hempstead, B. L., Schleifer, L. S. and Chao, M. V. (1989). Expression of functional nerve growth factor receptors after gene transfer. Science 243, 373-375.

Herrup, K. and Shooter, E. M. (1973). Properties of the β-nerve growth factor receptor of avian dorsal root ganglia. Proc. Natl Acad. Sci. USA 70, 3884-88.

Herrup, K. and Thoenen, H. (1979). Properties of the nerve growth factor receptor of a clonal line of rat pheochromocytoma (PC12) cells. Exp Cell Res 121, 71-8.

Heuer, J. G., S., F.-N., Wheeler, E. F. and Bothwell, M. (1990). Structure and developmental expression of the chicken NGF receptor. Dev Biol 137, 287-304.

Hohn, A., Leibrock, J., Bailey, K. and Barde, Y.-A. (1990). Identification and characterization of a novel member of the nerve growth factor/brain-derived neurotrophic factor family. Nature 344, 339-341.

Hosang, M. and Shooter, E. M. (1985). Molecular characteristics of nerve growth factor receptors on PC12 cells. J Biol Chem 260, 655-62.

Ibanez, C. F., Hallbook, F., Ebendal, T. and Persson, H. (1990). Structure-function studies of nerve growth factor: functional importance of highly conserved amino acid residues. EMBO J. 9,1477-1483.

Ibanez, C. F., Ebendal, T. and Persson, H. (1991a). Chimeric molecules with multiple neurotrophic activities reveal structural elements determining the specificities of NGF and BDNF. EMBO J. 10, 2105-2110.

Ibanez, C. F., Hallöök, F., Soderstrom, S., Ebendal, T. and Persson, H. (1991b). Biological and immunological properties of recombinant human, rat and chicken nerve growth factors: a comparative study. J. Neurochem. 57, 1033-1041.

Ip, N. Y., Ibanez, C. F., Nye, S. H., McClain, J., Jones, P. F., Gies, D. R., Belluscio, L., Le Beau, M. M., Espinosa III, R., Squinto, S. P., Persson, H. and Yancopoulos, G. (1992). Mammalian neurotrophin-4: structure, chromosomal localization, tissue distribution and receptor specificity. Proc Natl Acad Sci U S A, in press.

Johnson, D., Lanahan, A., Buck, C. R., Sehgal, A., Morgan, C., Mercer, E., Bothwell, M. and Chao, M. (1986). Expression and structure of the human NGF receptor. Cell 47, 545-554.

Kaplan, D., Hempstead, B., Martin-Zanca, D., Chao, M. and Parada, L. (1991a). The trk proto-oncogene product: a signal transducing receptor for nerve growth factor. Science 252, 554-558.

Kaplan, D., Martin-Zanca, D. and Parada, L. (1991b). Tyrosine phosphorylation and tyrosine kinase activity of the trk proto-oncogene product induced by NGF. Nature 350, 158-160.

Klein, R., Jing, S., Nanduri, V., O'Rourke, E. and Barbacid, M. (1991). The trk proto-oncogene encodes a receptor for nerve growth factor. Cell 65,189-197.

Leibrock, J., Lottspeich, A. H., Hofer, M., Hengerer, B., Masiakowski, P., Thoenen, H. and Barde, Y.-A.

(1989). Molecular cloning and expression of brain-derived neurotrophic factor. Nature 341,149–52.

Levi-Montalcini, R. and Angeletti, P. (1968). Nerve growth factor. Physiol. Rev. 48, 534–569.

Loeb, D., Maragos, J., Martin-Zanca, D., Chao, M., Parada, L. and Greene, L. (1991). The trk proto-oncogene rescues NGF responsiveness in mutant NGF nonresponsive PC12 cell lines. Cell 66, 961–966.

Longo, F., Vu, T.-K. H. and Mobley, W. (1990). The in vitro biological effect of nerve growth factor is inhibited by synthetic peptides. Cell Reg. 1,189–195.

Luthman, H. and Magnusson, G. (1983). High efficiency polyoma DNA transfection of chloroquine treated cells. Nucl. Acids Res. 11, 1295–1305.

Maisonpierre, P. C., Belluscio, L., S, S., Ip, N.Y., Furth, M. E., Lindsay, R. M. and Yancopoulos, G. D. (1990). Neurotrophin-3: A neurotrophic factor related to NGF and BDNF. Science 247,1446–1451.

Martin-Zanca, D., Oskam, R., Mitra, G., Copeland, T. and Barbacid, M. (1991). Molecular and biochemical characterization of the human ~rk proto-oncogene. Mol Cell Biol 9, 24–33.

McDonald, N. Q., Lapatto, R., Murray-Rust, J., Gunning, J., Wlodawer, A. and Blundell, T. L. (1991). New protein fold revealed by a 2.3-A resolution crystal structure of nerve growth factor. Nature 354, 411–414.

Meakin, S. and Shooter, E. (1991). Molecular investigations on the high-affinity nerve growth factor receptor. Neuron 6,153–163.

Meier, R., Becker-Andre, M., Gotz, R., Heumann, R., Shaw, A. and Thoenen, H. (1986). Molecular cloning of bovine and chick nerve growth factor (NGF): delineation of conserved and unconserved domains and their relationship to the biological activity and antigenicity of NGF. EMBO J. 5,1489–93.

Milbrandt, J. (1986). Nerve growth factor rapidly induces c-fos mRNA in PC12 rat pheochromocytoma cells. Proc Natl Acad Sci U S A 83, 4789–93.

Radeke, M. J., Misko, T. P., Hsu, C., Herzenberg, L. A. and Shooter, E. M. (1987). Gene transfer and molecular cloning of the rat nerve growth factor receptor. Nature 325, 593–597.

Richardson, P. M., Verge Issa, V. M. K. and Riopelle, R. J. (1986). Distribution of neuronal receptors for nerve growth factor in the rat. Neurosci. 6, 2312–2321.

Rodriguez-Tebar, A., Dechant, G. and Barde, Y.-A. (1990). Binding of brain derived neurotrophic factor to the nerve growth factor receptor. Neuron 4, 487492.

Rosenthal, A., Goeddel, D. V., Nguyen, T., Lewis, M., Shih, A., Laramee, G. R., Nikolics, K. and Winslow, J. W. (1990). Primary structure and biological activity of a novel human neurotrophic factor. Neuron 4, 767–773.

Sanger, F., Nicklen, S. and Coulson, A. R. (1977). DNA sequencing with chain terminating inhibitors. Proc. Natl. Acad. Sci. USA 74, 5463–7.

Sauve, K., Nachman, M., Spence, C., Bailon, P., Campbell, E., Tsien, W.-H., Kondas, J., Hakimi, J. and Ju, G. (1991). Localization in human interleukin 2 of the binding site to the (x chain (p55) of the interleukin 2 receptor. Proc Natl Acad Sci USA 88, 4636–4640.

Schwarz, M. A., Fisher, D., Bradshaw, R. A. and Isackson, P. J. (1989). Isolation and sequence of a cDNA clone of beta-nerve growth factor from the guinea pig prostate gland. J. Neurochem. 52, 1203–9.

Scott, J., Selby, M., Urdea, M., Quiroga, M., Bell, G. I. and Rutter, W. (1983). Isolation and nucleotide sequence of a cDNA encoding the precursor of mouse nerve growth factor. Nature 302, 538–40.

Selby, M. J., Edwards, R. H. and Rutter, W. J. (1987). Cobra nerve growth factor: structure and evolutionary comparison. J. Neurosci. Res. 18, 29314 8.

Sibanda, L., Blundell, T. and Thornton, J. (1989). Conformation of $\beta$-hairpins in protein structures. J Mol Biol 206, 759–777.

Squinto, S. P., Stitt, T. N., Aldrich, T. H., Davis, S., Bianco, S. M., Radziejewski, C., Glass, D. J., Masiakowski, P., Furth, M. E., Valenzuela, D. M., DiStefano, P. S., Yancopoulos, G. D. (1991). trkB encodes a functional receptor for brain-derived neurotrophic factor and neurotrophin-3 but not nerve growth factor. Cell 65, 885–993.

Suter, U., Heymach Jr, J. and Shooter, E. (1991). Two conserved domains in the NGF propeptide are necessary and sufficient for the biosynthesis of correctly processed and biologically active NGF. EMBO J 10, 2395–2400.

Sutter, A., Riopelle, R. J., Harris-Warrick, R. M. and Shooter, E. M. (1979). Nerve growth factor receptors: characterization of two distinct classes of binding sites on chick embryo sensory ganglia cells. J. Biol. Chem., 254, 5972–82.

Thoenen, H., Bandtlow, C. and Heumann, R. (1987). The physiological function of nerve growth factor in the central nervous system: comparison with the periphery. Rev. Physiol. Biochem. Pharmacol. 109,145–78.

Thoenen, H. and Barde, Y. A. (1980). Physiology of nerve growth factor. Physiol. Rev. 60, 1284–1325.

Ullrich, A., Gray, A., Berman, C. and Dull, T. J. (1983). Human $\beta$-nerve growth factor gene highly homologous to that of mouse. Nature 303, 821–25.

Weskamp, G. and Reichardt, L. (1991). Evidence that biological activity of NGF is mediated through a novel subclass of high affinity receptors. Neuron 6, 649–663.

Whittemore, S. R., Friedman, P. L., Larhammar, D., Persson, H., Gonzalez, C. M. and Holets, V. R. (1988). Rat beta-nerve growth factor sequence and site of synthesis in the adult hippocampus. J. Neurosci. Res. 20, 403–10.

Whittemore, S. R. and Seiger, A. (1987). The expression, localization and functional significance of beta-nerve growth factor in the central nervous system. Brain Res. 434, 439–64.

Yan, H., Schlessinger, J. and Chao, M. (1991). Chimeric NGF-EGF receptors define domains responsible for neuronal differentiation. Science 252, 561–564.

Yan, Q. and Johnson, E. (1988). An immunohistochemical study of the nerve growth factor receptor in developing rats. J Neurosci 8, 3481–98.

Yang, Y. C., Ciarlette, A. B., Temple, P. A., Chung, M. P., Kovacic, S., WitekGianotti, J. S., Leary, A. C., Kritz, R., Donahue, R. E., Wong, G. G. and Clark, S. C. (1986). Human IL-3 (multi-CSF): identification by expression cloning of a novel hematopoietic growth factor related to murine IL-3. Cell 47, 3–10.

We claim:

1. Mutant nerve growth factor having essentially the same biological activity as wild-type nerve growth factor, wherein at least one positively charged amino acid in amino acids 30 through 34 or amino acids 93 to 98 of wild-type nerve growth factor is replaced with an uncharged or negatively charged amino acid, wherein said replacement reduces the ability of the mutant nerve growth factor to bind $p75^{NGFR}$ as compared to wild-type nerve growth factor.

2. The mutant neurotrophic factor of claim 1 wherein Lys95 is replaced.

3. The mutant neurotrophic factor of claim 2 wherein said Lys95 is replaced by Ala.

4. The mutant neurotrophic factor of claim 1 wherein Lys32 is replaced.

5. The mutant neurotrophic factor of claim 4 wherein Lys34 is replaced.

6. The mutant neurotrophic factor of claim 4 wherein Lys95 is replaced.

7. The mutant neurotrophic factor of claim 1 wherein Lys34 is replaced.

8. A method of selecting for nerve growth factor mutants with reduced ability to bind $p75^{NGFR}$ comprising a) replacing a least one positively charged amino acid in amino acids 30 through 34 or amino acids 93 to 98 of the factor with an uncharged or negatively charged amino acid; and b) selecting those factors that demonstrate essentially the same biological activity as wild-type nerve growth molecule.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
        (A) LENGTH: 12 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:1:

```
Lys Thr Thr Ala Thr Asp Ile Lys Gly Lys Glu Val
 1               5                  10
```

(2) INFORMATION FOR SEQ ID NO:2:

(i) SEQUENCE CHARACTERISTICS:
        (A) LENGTH: 12 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:2:

```
Lys Thr Lys Ala Thr Asp Ile Lys Gly Lys Glu Val
 1               5                  10
```

(2) INFORMATION FOR SEQ ID NO:3:

(i) SEQUENCE CHARACTERISTICS:
        (A) LENGTH: 12 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:3:

```
Lys Thr Thr Ala Thr Asp Ile Lys Gly Asn Thr Val
 1               5                  10
```

(2) INFORMATION FOR SEQ ID NO:4:

(i) SEQUENCE CHARACTERISTICS:
        (A) LENGTH: 12 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:4:

```
Lys Lys Thr Ala Val Asp Met Ser Gly Gly Thr Val
 1               5                  10
```

(2) INFORMATION FOR SEQ ID NO:5:

(i) SEQUENCE CHARACTERISTICS:
        (A) LENGTH: 12 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:5:

-continued

Lys Thr Ser Ala Ile Asp Ile Arg Gly His Gln Val
1 5 10

( 2 ) INFORMATION FOR SEQ ID NO:6:

( i ) SEQUENCE CHARACTERISTICS:
( A ) LENGTH: 12 amino acids
( B ) TYPE: amino acid
( C ) STRANDEDNESS: single
( D ) TOPOLOGY: unknown ( i i ) MOLECULE TYPE: peptide ( x i ) SEQUENCE DESCRIPTION: SEQ ID NO:6:

Lys Arg Thr Ala Val Asp Asp Arg Gly Lys Ile Val
1 5 10